US009803220B2

(12) United States Patent
Marliere et al.

(10) Patent No.: US 9,803,220 B2
(45) Date of Patent: Oct. 31, 2017

(54) PRODUCTION OF ALKENES FROM 3-HYDROXY-1-CARBOXYLIC ACIDS VIA 3-SULFONYLOXY-1-CARBOXYLIC ACIDS

(71) Applicants: Scientist of Fortune S.A., Luxembourg (LU); Global Bioenergies, Evry (FR)

(72) Inventors: Philippe Marliere, Tournai (BE); Maria Anissimova, Nozay (FR); Mathieu Allard, Saint-Vrain (FR)

(73) Assignees: Global Bioenergies, Evry (FR); Scientist of Fortune, S.A., Luxembourg (LU)

( * ) Notice: Subject to any disclaimer, the term of this patent is extended or adjusted under 35 U.S.C. 154(b) by 0 days.

(21) Appl. No.: 14/438,295

(22) PCT Filed: Oct. 24, 2013

(86) PCT No.: PCT/EP2013/072278
§ 371 (c)(1),
(2) Date: Apr. 24, 2015

(87) PCT Pub. No.: WO2014/064198
PCT Pub. Date: May 1, 2014

(65) Prior Publication Data
US 2015/0291981 A1    Oct. 15, 2015

(30) Foreign Application Priority Data

Oct. 25, 2012  (EP) .................................. 12190039

(51) Int. Cl.
C12P 5/02    (2006.01)
C12N 9/10    (2006.01)

(52) U.S. Cl.
CPC ................ *C12P 5/026* (2013.01); *C12N 9/13* (2013.01)

(58) Field of Classification Search
CPC ... C12N 9/16; C12N 9/13; C12P 5/026; Y02P 20/52
See application file for complete search history.

(56) References Cited

U.S. PATENT DOCUMENTS

| 6,255,088 | B1 | 7/2001 | Wong et al. | |
| 8,765,431 | B2 * | 7/2014 | Sherman | C12N 9/16 435/166 |
| 9,453,244 | B2 * | 9/2016 | Marliere | C12N 9/1085 |

(Continued)

FOREIGN PATENT DOCUMENTS

| EP | 1132391 A1 | 9/2001 | |
| WO | WO 2011/011689 * | 1/2011 | ................ C12P 7/64 |
| WO | 2012052427 A | 4/2012 | |

OTHER PUBLICATIONS

Allen et al., Kinetics of reaction of metal alkyl compounds with alkenes. Part 2.—Aluminium triethyl, Trans. Faraday Soc. (1967), vol. 63, pp. 1636-1646.*

(Continued)

*Primary Examiner* — Alexander Kim
(74) *Attorney, Agent, or Firm* — Michele Wales; InHouse Patent Counsel, LLC

(57) ABSTRACT

The application describes a method for producing alkenes (for example propylene, ethylene, 1-butylene, isobutylene, isoamylene, butadiene or isoprene) from 3-hydroxy-1-carboxylic acids via 3-sulfonyloxy-1-carboxylic acids.

Figure 1A:
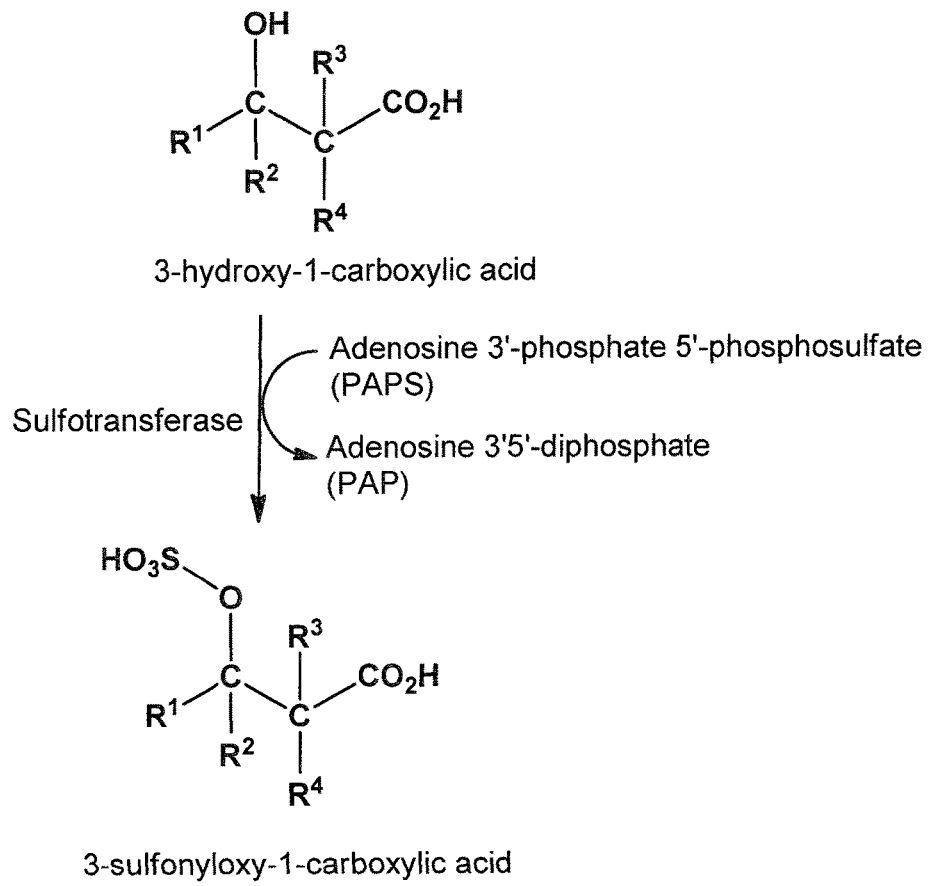

16 Claims, 7 Drawing Sheets 3-hydroxy-1-carboxylic acid 3-hydroxy-1-carboxylic acid 3-sulfonyloxy-1-carboxylic acid 3-sulfonyloxy-1-carboxylic acid

(56) References Cited

U.S. PATENT DOCUMENTS

2011/0091952 A1* 4/2011 Sherman ................ C12N 9/16
 435/166
2015/0284743 A1* 10/2015 Marliere ............. C12N 9/1205
 435/167

OTHER PUBLICATIONS

Written Opinion in parent PCT application PCT/EP2013/072278.
International Search Report received in PCT/EP2013/072278.
Office of Action dated Jun. 8, 2017 received in corresponding Chinese Patent Application for Invention No. 201380055899.0. (along with English Language translation).
Pakhomova, et al., "The Structures of the Unique Sulfotransferase Retinol Dehydratase with Product and Inhibitors Provide Insight into Enzyme Mechanism and Inhibition", Protein Science, vol. 14, pp. 176-182, (2005).
Wang Y. G. et al. Organic Chemistry (2nd ed.) Chemical Industry Press, p. 278, published on Jan. 31, 2009. (English Translation also provided).
Yuan, L. B. Guidance for Learning Organic Chemistry. Liaoning Science and Technology Publishing House, first edition in Nov. 1985, p. 19-21, published on Nov. 30, 1985, (English Translation also provided).

* cited by examiner

PRODUCTION OF ALKENES FROM 3-HYDROXY-1-CARBOXYLIC ACIDS VIA 3-SULFONYLOXY-1-CARBOXYLIC ACIDS

This Application is a 35 U.S.C. 371 National Phase filing of PCT/EP2013/072278, filed Oct. 24, 2013, which is a continuation of EP 12 190 039 which was filed on Oct. 25, 2012, which are incorporated by reference in their entirety.

The present invention relates to a method for generating alkenes through a biological process. More specifically, the invention relates to a method for producing alkenes (for example propylene, ethylene, 1-butylene, isobutylene, isoamylene, butadiene or isoprene) from 3-hydroxy-1-carboxylic acids via 3-sulfonyloxy-1-carboxylic acids.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels.

Ethylene, the simplest alkene, lies at the heart of industrial organic chemistry: it is the most widely produced organic compound in the world. It is used in particular to produce polyethylene, a major plastic. Ethylene can also be converted to many industrially useful products by reaction (of oxidation, of halogenation).

Propylene holds a similarly important role: its polymerization results in a plastic material, polypropylene. The technical properties of this product in terms of resistance, density, solidity, deformability, and transparency are unequalled. The worldwide production of polypropylene has grown continuously since its invention in 1954.

Butylene exists in four forms, one of which, isobutylene, enters into the composition of methyl-tert-butyl-ether (MTBE), an anti-knock additive for automobile fuel. Isobutylene can also be used to produce isooctene, which in turn can be reduced to isooctane (2,2,4-trimethylpentane); the very high octane rating of isooctane makes it the best fuel for so-called "gasoline" engines.

Amylene, hexene and heptene exist in many forms according to the position and configuration of the double bond. These products have real industrial applications but are less important than ethylene, propylene or butenes.

All these alkenes are currently produced by catalytic cracking of petroleum products (or by a derivative of the Fisher-Tropsch process in the case of hexene, from coal or gas). Their cost is therefore naturally indexed to the price of oil. Moreover, catalytic cracking is sometimes associated with considerable technical difficulties which increase process complexity and production costs.

In the alkene chemical family, isoprene (2-methyl-1,3-butadiene) is the terpene motif which, through polymerization, leads to rubber. Other terpenes might be developed, by chemical, biological or mixed pathways, as usable products such as biofuels or to manufacture plastics.

The production of alkenes, in particular terminal alkenes (ethylene mono- or di-substituted at position 2: $H_2C=C(R^1)(R^2)$) has apparently been less extensively investigated. The conversion of isovalerate to isobutylene by the yeast *Rhodotorula minuta* has been described (Fujii T. et al., Appl. Environ. Microbiol., 1988, 54:583), but the efficiency of this reaction, characterized by a very low value of the turnover number ($k_{cat}$ is $1\times10^{-5}$ sec$^{-1}$), is far from permitting an industrial application. Large-scale biosynthesis of isobutylene by this pathway seems highly unfavorable, since it would require the synthesis and degradation of one molecule of leucine to form one molecule of isobutylene. Also, the enzyme catalyzing the reaction uses heme as cofactor, poorly lending itself to recombinant expression in bacteria and to improvement of enzyme parameters. Other microorganisms have been described as being marginally capable of naturally producing isobutylene from isovalerate; the yields obtained are even lower than those obtained with *Rhodotorula minuta* (Fukuda H. et al, Agric. Biol. Chem., 1984, 48:1679).

The same studies have also described the natural production of propylene: many microorganisms are capable of producing propylene, once again with an extremely low yield. The production of ethylene by plants has long been known (Meigh et al, 1960, Nature, 186:902). According to the metabolic pathway elucidated, methionine is the precursor of ethylene (Adams and Yang, PNAS, 1979, 76:170). Conversion of 2-oxoglutarate has also been described (Ladygina N et al., Process Biochemistry 2006, 41:1001). Since the production of a two-carbon molecule of ethylene consumes a four- or five-carbon molecule precursor, these pathways appear materially and energetically unfavorable for their industrial application.

WO2010/001078 describes a process for producing alkenes by enzymatic conversion of 3-hydroxyalkanoic acids with an enzyme having the activity of a decarboxylase. Such a method is advantageous because it helps to avoid the use of petroleum products, to lower the costs of producing plastics and fuels and can have a considerable global environmental impact by allowing carbon to be stored in solid form. Although the method described in WO 2010/001078 allows to produce alkenes by enzymatic reactions, there is still a need for further methods allowing the production of alkenes in biological systems which can be extended to an industrial scale. The present application addresses this need.

The present invention relates to a method for producing an alkene characterized in that it comprises the conversion of a 3-hydroxy-1-carboxylic acid through a biological process, in particular an enzymatic process, wherein a 3-hydroxy-1-carboxylic acid is, in a first step, enzymatically converted into a 3-sulfonyloxy-1-carboxylic acid and wherein the thus produced 3-sulfonyloxy-1-carboxylic acid is subsequently converted into the alkene. The enzymatic conversion of the 3-hydroxy-1-carboxylic acid in the first step into a 3-sulfonyloxy-1-carboxylic acid comprises a sulfate transfer (sulfurylation). The conversion of the produced 3-sulfonyloxy-1-carboxylic acid into the alkene comprises a desulfurylation/decarboxylation. This second conversion can either be achieved by a thermal conversion or by an enzymatic reaction as will be explained in more detail below.

The term "3-hydroxy-1-carboxylic acid", as used herein, denotes a molecule responding to the following general formula I:

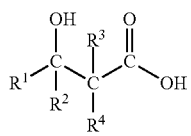

Formula I in which $R^1$ and $R^3$ are independently selected from hydrogen (—H), methyl (—CH3), ethyl (—CH2-CH3), isopropyl (—CH2(CH3)2), vinyl (—CH=CH2) and isopropenyl (—C(CH3)=CH2) and in which $R^2$ and $R^4$ are independently selected from hydrogen (—H) and methyl (—CH3).

The term "3-sulfonyloxy-1-carboxylic acid" denotes a molecule which responds to the following general formula II:

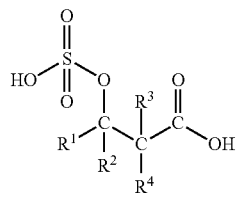

Formula II in which $R^1$, $R^2$, $R^3$ and $R^4$ have the same meaning as specified above in connection with formula I.

The alkene produced by the method according to the present invention is a molecule which responds to the following general formula III:

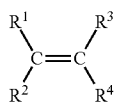

Formula III in which $R^1$, $R^2$, $R^3$ and $R^4$ have the same meaning as specified above in connection with formula I.

In preferred embodiments the 3-hydroxy-1-carboxylic acid which is converted in the method according to the invention is selected from a 3-hydroxy-1-carboxylic acid as specified in the following Table 1 and is converted into a corresponding alkene as indicated in Table 1.

TABLE 1

| 3-hydroxy-1-carboxylic acid | | Corresponding alkene | |
|---|---|---|---|
| name | formula | name | formula |
| 3-hydroxypropionate | HOCH₂—CH₂—CO₂H | ethylene | H₂C=CH₂ |
| 3-hydroxybutyrate | CH₃—CH(OH)—CH₂—CO₂H | propylene | H₃C—CH=CH₂ |
| 2-methyl-3-hydroxypropionate | HOCH₂—CH(CH₃)—CO₂H | propylene | H₃C—CH=CH₂ |
| 3-hydroxypentanoate | CH₃—CH₂—CH(OH)—CH₂—CO₂H | but-1-ene | H₃C—CH₂—CH=CH₂ |
| 2-(hydroxymethyl)butyrate | HOCH₂—CH(CH₂CH₃)—CO₂H | but-1-ene | H₃C—CH₂—CH=CH₂ |
| 2-methyl-3-hydroxybutyrate | CH₃—CH(OH)—CH(CH₃)—CO₂H | (Z) but-2-ene | H₃C—CH=CH—CH₃ (Z) |
| 2-methyl-3-hydroxybutyrate | CH₃—CH(OH)—CH(CH₃)—CO₂H | (E) but-2-ene | H₃C—CH=CH—CH₃ (E) |

TABLE 1-continued

| 3-hydroxy-1-carboxylic acid | | Corresponding alkene | |
|---|---|---|---|
| name | formula | name | formula |
| 3-hydroxy-3-methylbutyrate | (H$_3$C)(CH$_3$)C(OH)–CH(H)–CO$_2$H | 2-methylpropylene aka isobutene | (H$_3$C)(H$_3$C)C=CH$_2$ |
| 2,2-dimethyl-3-hydroxypropionate | HOCH$_2$–C(CH$_3$)(CH$_3$)–CO$_2$H | 2-methylpropylene aka isobutene | (H$_3$C)(H$_3$C)C=CH$_2$ |
| 2-methyl-3-hydroxypentanoate | H$_3$C–CH$_2$–CH(OH)–CH(CH$_3$)–CO$_2$H | (Z) pent-2-ene aka (Z) 2-amylene | H$_3$C–HC=CH–CH$_2$–CH$_3$ |
| 2-ethyl-3-hydroxybutyrate | H$_3$C–CH(OH)–C(CH$_2$CH$_3$)(H)–CO$_2$H | (Z) pent-2-ene aka (Z) 2-amylene | H$_3$C–HC=CH–CH$_2$–CH$_3$ |
| 2-methyl-3-hydroxypentanoate | H$_3$C–CH$_2$–CH(OH)–CH(CH$_3$)–CO$_2$H | (E) pent-2-ene aka (E) 2-amylene | H$_3$C–HC=CH–CH$_2$–CH$_3$ |
| 2-ethyl-3-hydroxybutyrate | H$_3$C–CH(OH)–C(CH$_2$CH$_3$)(H)–CO$_2$H | (E) pent-2-ene aka (E) 2-amylene | H$_3$C–HC=CH–CH$_2$–CH$_3$ |
| 2,3-dimethyl-3-hydroxybutyrate | (H$_3$C)(CH$_3$)C(OH)–CH(CH$_3$)–CO$_2$H | 2-methylbut-2-ene aka isoamylene | (H$_3$C)(H$_3$C)C=CH(CH$_3$) |
| 2,2-dimethyl-3-hydroxybutyrate | H$_3$C–CH(OH)–C(CH$_3$)(CH$_3$)–CO$_2$H | 2-methylbut-2-ene aka isoamylene | (H$_3$C)(H$_3$C)C=CH(CH$_3$) |
| 3-methyl-3-hydroxypentanote | H$_3$C–CH$_2$–C(OH)(CH$_3$)–CH(H)–CO$_2$H | 2-methylbut-1-ene | H$_2$C=C(CH$_3$)–CH$_2$–CH$_3$ |
| 2-methyl-2-(hydroxymethyl)butyrate | HOCH$_2$–C(CH$_3$)(CH$_2$CH$_3$)–CO$_2$H (H on α) | 2-methylbut-1-ene | H$_2$C=C(CH$_3$)–CH$_2$–CH$_3$ |

TABLE 1-continued

| 3-hydroxy-1-carboxylic acid | | Corresponding alkene | |
|---|---|---|---|
| name | formula | name | formula |
| 4-methyl-3-hydroxypentanote | (structure) | 3-methylbut-1-ene | (structure) |
| 2-(hydroxymethyl)-3-methylbutyrate | (structure) | 3-methylbut-1-ene | (structure) |
| 3-hydroxypent-4-enoate | (structure) | 1,3-butadiene | (structure) |
| 2-(hydroxymethyl)but-3-enoate | (structure) | 1,3-butadiene | (structure) |
| 3-hydroxy-4-methylpent-4-enoate | (structure) | 2-methyl-1,3-butadiene aka isoprene | (structure) |
| 3-hydroxy-3-methylpent-4-enoate | (structure) | 2-methyl-1,3-butadiene aka isoprene | (structure) |
| 2-(hydroxymethyl)-2-methylbut-3-enoate | (structure) | 2-methyl-1,3-butadiene aka isoprene | (structure) |
| 2-(hydroxymethyl)-3-methylbut-3-enoate | (structure) | 2-methyl-1,3-butadiene aka isoprene | (structure) |

As described above, according to the method of the invention a 3-hydroxy-1-carboxylic acid is first converted into a 3-sulfonyloxy-1-carboxylic acid. This is achieved by a sulfurylation reaction, i.e. a reaction in which a sulfate group is transferred to the hydroxyl group at position 3 of the 3-hydroxy-1-carboxylic acid.

The conversion of the 3-hydroxy-1-carboxylic acid into the 3-sulfonyloxy-1-carboxylic acid according to the method of the present invention can preferably be achieved by an enzymatic reaction, in particular by the use of an enzyme which catalyzes the transfer of a sulfate group onto a molecule, such as sulfotransferases. Sulfotransferases are described e.g. in Cleland and Hengge (Chem. Rev. 106 (2006), 3252-3278).

For example, enzymes which can be employed in this reaction are enzymes which are classified as E.C. 2.8.2, i.e. transferase enzymes that catalyze the transfer of a sulfate group from a donor molecule to an acceptor alcohol or amine. Preferably, PAPS (adenosine 3'-phosphate 5'-phosphosulfate) or APS (adenosine 5'-phosphosulfate) is the donor of the sulfate group in such a reaction.

Figure 1B:
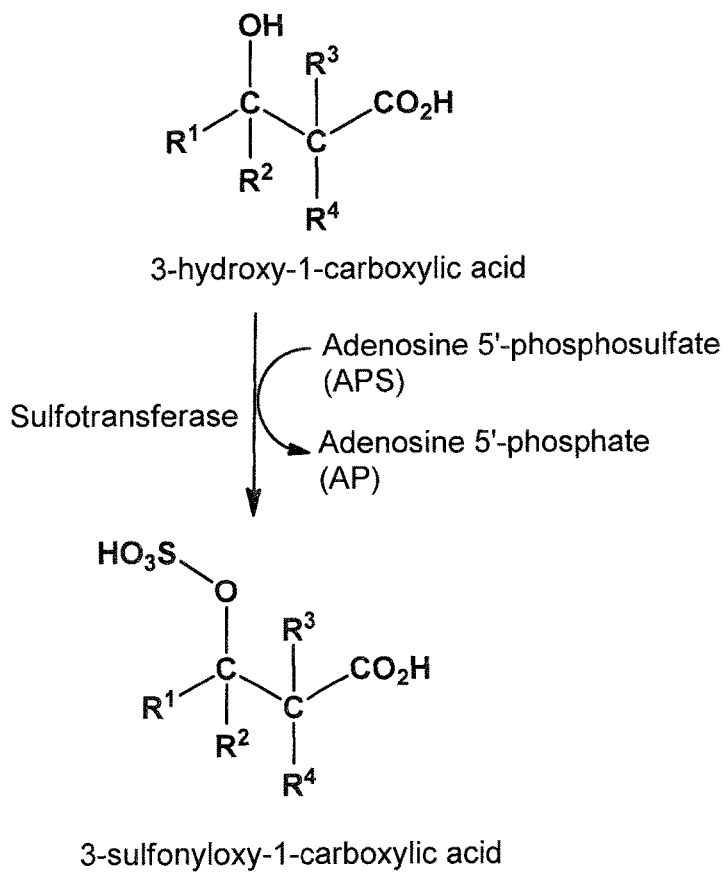

The general reaction scheme for converting, according to the method of the present invention, a 3-hydroxy-1-carboxylic acid into a 3-sulfonyloxy-1-carboxylic acid by employing a sulfotransferase and PAPS or APS as a co-factor is shown in FIG. 1.

In principle, any sulfotransferase can be used. In a preferred embodiment the sulfotransferase is an alcohol sulfotransferase (EC 2.8.2.2), a steroid sulfotransferase (EC 2.8.2.15), a scymnol sulfotransferase (EC 2.8.2.32), a flavonol 3-sulfotransferase (EC 2.8.2.25), a retinol sulfotransferase/dehydratase, a PKS sulfotransferase (ST) or an OLS sulfotransferase ST.

Thus, in one preferred embodiment the enzymatic conversion of the 3-hydroxy-1-carboxylic acid into a corresponding 3-sulfonyloxy-1-carboxylic acid can, e.g., be achieved by the use of an alcohol sulfotransferase (EC 2.8.2.2). Alcohol sulfotransferases are enzymes which catalyze the following reaction:

3'-phosphoadenylyl sulfate (PAPS)+an alcohol
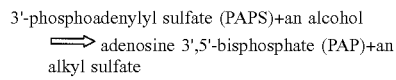 adenosine 3',5'-bisphosphate (PAP)+an alkyl sulfate The occurrence of these enzymes has been described for a number of organisms, e.g. for *E. coli, Oryctolagus cuniculus, Petromyzon marinus, Rana catesbeiana, Rattus norvegicus, Mus musculus, Cavia porcellus, Mesocricetus auratus, Sus scrofa, Drosophila melanogaster* and *Homo sapiens*. In principle, any known alcohol sulfotransferase can be employed in the method according to the invention. In one aspect of the present invention, a alcohol sulfotransferase of mammalian origin is used, such as a alcohol sulfotransferase from an organism belonging to the genus *Rattus*, preferably of the species *Rattus norvegicus* (Lyon and Jakoby; Arch. Biochem. Biophys. 202 (1980), 474-481).

In another preferred embodiment the enzymatic conversion of the 3-hydroxy-1-carboxylic acid into a corresponding 3-sulfonyloxy-1-carboxylic acid can, e.g., be achieved by the use of a steroid sulfotransferase (EC 2.8.2.15). Steroid sulfotransferases are enzymes which catalyze the following reaction:

3'-phosphoadenylyl sulfate (PAPS)+a phenolic steroid 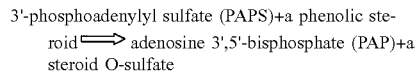 adenosine 3',5'-bisphosphate (PAP)+a steroid O-sulfate The occurrence of these enzymes has been described for a number of organisms, e.g. for *Rattus norvegicus, Mus musculus, Cavia porcellus, Sus scrofa, Danio rerio, Bos Taurus, Brassica napus* and *Homo sapiens*. In principle, any known steroid sulfotransferase can be employed in the method according to the invention.

In another preferred embodiment enzymatic conversion of the 3-hydroxy-1-carboxylic acid into a corresponding 3-sulfonyloxy-1-carboxylic acid can, e.g., be achieved by the use of a hydroxysteroid sulfotransferase as described, e.g., in Lyon and Jakoby (Arch. Biochem. Biophys. 202 (1980), 474-481).

In another preferred embodiment the enzymatic conversion of the 3-hydroxy-1-carboxylic acid into a corresponding 3-sulfonyloxy-1-carboxylic acid can, e.g., be achieved by the use of a scymnol sulfotransferase (EC 2.8.2.32). Scymnol sulfotransferases are enzymes which catalyze the following reaction:

3'-phosphoadenylyl sulfate (PAPS)+5-beta scymnol
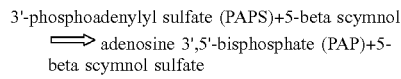 adenosine 3',5'-bisphosphate (PAP)+5-beta scymnol sulfate The occurrence of these enzymes has been described for some organisms, e.g. for *Heterodontus portusjacksoni, Trygonorrhina fasciata* and *Trygonoptera* sp. In principle, any known scymnol sulfotransferase can be employed in the method according to the invention.

In another preferred embodiment the enzymatic conversion of the 3-hydroxy-1-carboxylic acid into a corresponding 3-sulfonyloxy-1-carboxylic acid can, e.g., be achieved by the use of a flavonol 3-sulfotransferase (EC 2.8.2.25). Flavonol sulfotransferases are enzymes which catalyze the following reaction:

3'-phosphoadenylyl sulfate (PAPS)+quercetin
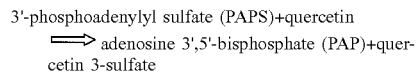 adenosine 3',5'-bisphosphate (PAP)+quercetin 3-sulfate Apart from quercetin, these enzymes also accept other flavonol aglycones as substrate.

The occurrence of these enzymes has been described for some organisms, e.g. for *Flaveria chlorifolia* and *Flavera bidentis*. In principle, any known flavonol sulfotransferase can be employed in the method according to the invention.

In another preferred embodiment the enzymatic conversion of the 3-hydroxy-1-carboxylic acid into a corresponding 3-sulfonyloxy-1-carboxylic acid can, e.g., be achieved by the use of an enzyme which is classified as a retinol sulfotransferase/dehydratase. This enzyme is, e.g., described in Pakhomova et al. (Protein Science 14 (2005), 176-182) and in Vakiani et al. (J. Biol. Chem. 273 (1998), 35381-35387). This enzyme catalyzes the conversion of retinol to the retro-retinoid anhydro-retinol according to the following reaction:

Retinol+PAPS=>retinyl sulfate+PAP=>anhydroretinol

It belongs to the sulfotransferase superfamily but shows some unique features that distinguish it from other members of this superfamily. It has only a very low sequence homology to the most homologous sulfotransferase rat aryl sulfotransferase (30%) and it is significantly larger (41 kDa) than mammalian sulfotransferases (30-36 kDa). It is a typical cytosolic sulfotransferase and sulfonates a wide variety of different hydroxycompounds, such as p-nitrophenol, phenol, vanillin and serotonin. The feature that most distinguishes the enzyme from other sulfotransferases is that the end product of the enzymatic reaction, anhydroretinol, is not sulfonated. Retinyl sulfate appears to be a transient intermediate in the transformation of retinol to anhydroretinol.

In a preferred embodiment the retinol sulfotransferase/dehydratase employed in a method according to the invention is a retinol sulfotransferase/dehydratase from *Spodoptera frugiperda*.

In another preferred embodiment the enzymatic conversion of the 3-hydroxy-1-carboxylic acid into a corresponding 3-sulfonyloxy-1-carboxylic acid can, e.g., be achieved by the use of the sulfotransferase (ST) domain from the CurM polyketide synthase (PKS) from the curacin A biosynthetic pathway (referred to as PKS sulfotransferase (ST)) of *Moorea producens* (formerly *Lyngbya majuscala*) or the sulfotransferase (ST) domain of the olefin synthase (OLS) from the hydrocarbon-producing system of *Synechococcus* PCC 7002 (referred to as OLS sulfotransferase (ST)). These two sulfotransferases are "activating" sulfotransferases that, in their natural function, sulfonate beta-hydroxyacyl thioester substrates. The CurM polyketide synthase (PKS) ST domain from the curacin A biosynthetic pathway of *Moorea producens* and the olefin synthase (OLS) ST from the hydrocarbon-producing system of *Synechococcus* PCC 7002 both are part of a tridomain containing an acyl carrier protein (ACP), the ST and a thioesterase (TE). The mechanism of action of these "activating" sulfotransferases is described, e.g., in McCarthy et al. (ACS Chem. Biol. (Sep. 26, 2012; electronic publication ahead of print) and in Mendez-Perez et al. (Appl. Env. Microbiol. 77 (2011), 4264-4267). In a preferred embodiment, the PKS sulfotransferase (ST) employed in the method according to the present invention is a protein having the sequence as available in Uniprot accession number D0E8E2 (residues 1604 to 1917). In another preferred embodiment, the OLS sulfotransferase (ST) employed in the method according to the present invention is a protein having the sequence as available in Uniprot accession number B1XKC6 (residues 2118 to 2430).

However, it is not only possible to use in a method according to the present invention the ST domains of the two above mentioned specific enzymes PKS or OLS but also sulfotransferase which are highly homologous to these ST domains, e.g. which show more than 50%, preferably more than 70%, even more preferably more than 80%, particularly preferred more than 90% sequence identity and which show the same enzymatic activity. Accordingly, the term PKS or OLS sulfotransferase (ST) also means enzymes which show the above mentioned sequence identity and the same enzymatic activity.

As described above, the obtained 3-sulfonyloxy-1-carboxylic acid is, according to the method of the present invention, further converted into a corresponding alkene. This conversion is achieved by a desulfurylation/decarboxylation reaction in which $H_2SO_4$ and $CO_2$ are set free. This conversion can be achieved in different manners.

Figure 2:
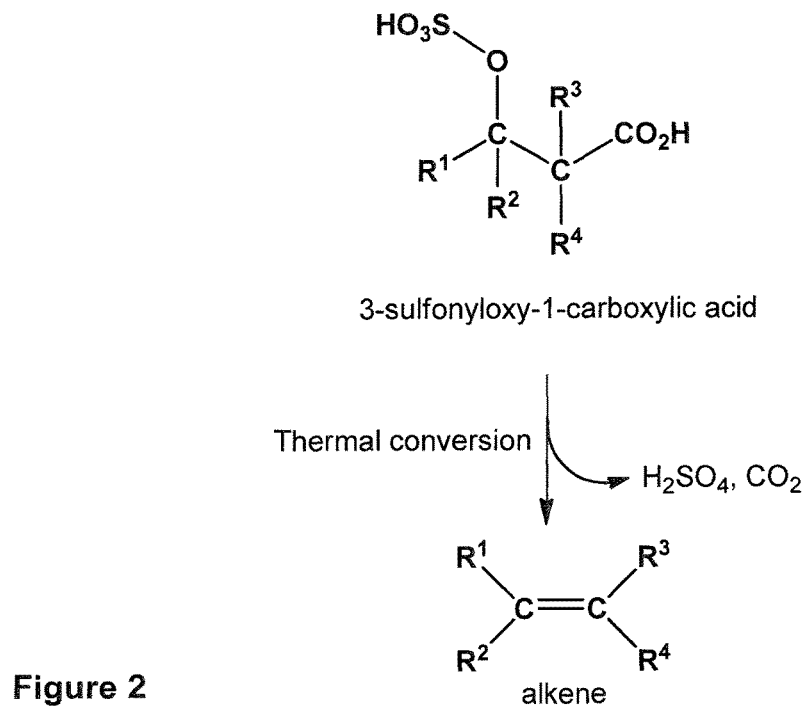

In a first aspect of the method according to the invention, the conversion of the 3-sulfonyloxy-1-carboxylic acid into a corresponding alkene is achieved by a thermal conversion. FIG. 2 shows a scheme of this conversion. "Thermal conversion" in this context means that the 3-sulfonyloxy-1-carboxylic acid is incubated at elevated temperatures. It could be shown by the inventors that incubation of a 3-sulfonyloxy-1-carboxylic acid according to formula II at elevated temperatures leads to a significant conversion of the 3-sulfonyloxy-1-carboxylic acid into the corresponding alkene. The term "elevated temperature" means a temperature which is higher than room temperature, preferably 30° C. or higher and more preferably about 37° C. or higher. As is evident from the appended Examples, the conversion of sulfonylbutyrate into propylene already occurs at 37° C. Thus, for some embodiments of the method according to the invention an elevated temperature of 30° C. or higher and preferably about 37° C. or higher suffices to achieve an efficient conversion. This opens up the possibility to employ in a method according to the invention mesophilic (micro) organisms which can be cultured at these temperatures, such as e.g. *E. coli*. In other embodiments higher temperatures may be necessary to achieve the conversion of the 3-sulfonyloxy-1-carboxylic acid into a corresponding alkene. Accordingly, in other preferred embodiments the term "elevated temperature" means a temperature which is 40° C. or higher, more preferably 45° C. or higher, even more preferably 50° C. or higher, 55° C. or higher, 60° C. or higher and particularly preferred 65° C. or higher.

Figure 3:
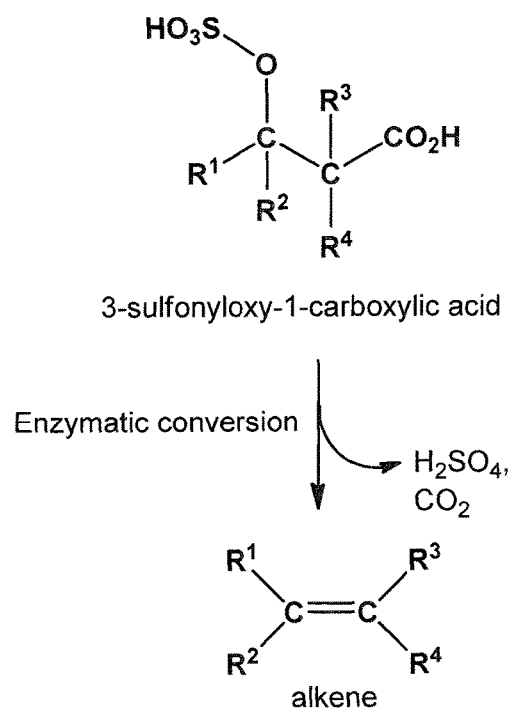

In another aspect of the method according to the invention, the conversion of the 3-sulfonyloxy-1-carboxylic acid into a corresponding alkene is achieved by an enzymatic desulfurylation/decarboxylation, i.e. the desulfurylation/decarboxylation is achieved by employing an enzyme. FIG. 3 shows a scheme of this conversion.

Different types of enzymes can be used in order to achieve this desulfurylation/decarboxylation. In one embodiment of the method according to the invention, the conversion of the 3-sulfonyloxy-1-carboxylic acid into a corresponding alkene is achieved by the use of an enzyme which is classified as a diphosphomevalonate decarboxylase or is an enzyme which is derived from such an enzyme and which has the capacity to convert a 3-sulfonyloxy-1-carboxylic acid as defined herein above into a corresponding alkene. Diphosphomevalonate decarboxylase is an enzyme which is considered by NCBI or an equivalent engine as having a COG3407 domain. It is classified in the EC number EC 4.1.1.33. A diphosphomevalonate decarboxylase is able to catalyze the decarboxylation of mevalonate diphosphate. In this reaction ATP and 5-diphosphomevalonate are converted into ADP, phosphate, isoprenyl pyrophosphate and $CO_2$. The activity of a diphosphomevalonate decarboxylase can be measured according to methods known in the art, e.g. as described in Reardon et al. (Biochemistry 26 (1987), 4717-4722). It has been reported that at least in some cases the reaction is divalent cation-dependent (see, e.g., Krepkiy et al., Protein Science 13 (2004), 1875-1881; Michihara et al., Biol. Pharm. Bull. 25 (2002), 302-306).

Diphosphomevalonate decarboxylase is an enzyme which, in its natural function, is part of the mevalonate pathway for isoprenoid synthesis in bacteria and of the sterol biosynthesis pathway in eukaryotes. It has been identified and isolated from various organisms such as animals, fungi, yeasts and bacteria. It is also expressed by certain plants (Lalitha et al., Phytochemistry 24 (11), (1985), 2569-2571). Many genes encoding this enzyme have been cloned and sequenced. These enzymes are generally composed of 300 to 400 amino acids and use ATP as co-substrate, which is converted during the reaction to ADP and inorganic phosphate. The phosphate group is transferred from the ATP molecule to the tertiary alcohol of mevalonate diphosphate, releasing ADP. The reaction intermediate phosphorylated on the 3-hydroxyl group then undergoes elimination of the phosphate group, in the physiological case releasing isopentenyl diphosphate.

The three-dimensional structure of several diphosphomevalonate decarboxylases has already been determined (see, e.g., Byres et al. (J. Mol. Biol. 371 (2007), 540-553); Bonanno et al. (Proc. Natl Acad. Sci. USA 98 (2001), 12896-12901)) and considerable knowledge is available about its active site, amino acid residues crucial for the catalytic reaction and the actual enzymatic reaction (see, e.g. Byres et al. (J. Mol. Biol. 371 (2007), 540-553); Bonanno et al. (Proc. Natl Acad. Sci. USA 98 (2001), 12896-12901)). In most cases the enzyme is composed of about 300 to 400 amino acids and uses ATP as cosubstrate which is converted during the decarboxylation reaction into ATP and inorganic phosphate.

Diphosphomevalonate decarboxylases have been described for various organisms and also amino acid and nucleotide sequences encoding them are available for numerous sources.

In principle any diphosphomevalonate decarboxylase can be used in the context of the present invention, in particular from prokaryotic or eukaryotic organisms. Eukaryotic diphosphomevalonate decarboxylases are described, for example, for animals such as *Rattus norvegicus, Gallus gallus, Homo sapiens, Mus musculus, Sus scrofa, D. melanogaster, C. elegans* and *Trypanosoma brucei*, for plants such as *Arabidopsis thaliana, Ginko biloba, Oryza sativa, Pisum sativum*, for yeasts, such as *Saccharomyces cerevisiae* and *Candida albicans*. Also numerous prokaryotic diphosphomevalonate decarboxylases have been described, e.g. for *Helicobacter, Staphylococcus aureus, Streptococcus pneumoniae, Enterococcus faecium, Listeria monocytgenes, Leuconostoc citreum, Lactobacillus reuteri*, to name just some. Table 2 provides a list of sequences of diphosphomevalonate decarboxylases from different organisms indicating the accession numbers under which they can be retrieved from the respective databases.

TABLE 2

| Organism | Genebank or Uniprot Accession number |
| --- | --- |
| Bombyx mori | A5A7A2 |
| Saccharomyces cerevisiae strain YJM7 | A6ZSB7 |
| Solanum lycopersicum | A8WBX7 |
| Hevea brasiliensis | A9ZN03 |
| Nicotiana langsdorffii × Nicotiana sanderae | B3F8H5 |
| Saccharomyces cerevisiae (strain RM11-1a) | B3LPK0 |
| Phaeodactylum tricornutum CCAP 1055 | B7S422 |
| Candida dubliniensis | B9W6G7 |
| Pichia pastoris | C4QX63 |
| Ashbya gossypii | Q751D8 |
| Bos taurus | Q0P570 |
| Danio rerio | Q5U403 |
| Debaryomyces hanseni | Q6BY07 |
| Dictyostelium discoideum | Q54YQ9 |
| Homo sapiens | P53602 |
| Mus musculus | Q99JF5 |
| Rattus norvegicus | Q62967 |
| Schizosaccharomyces pombe | O13963 |
| Saccharomyces cerevisiae | P32377 |
| Arnebia euchroma | Q09RL4 |
| Aspergillus oryzae | Q2UGF4 |
| Mus musculus | Q3UYC1 |
| Ginkgo biloba | Q5UCT8 |
| Rattus norvegicus | Q642E5 |
| Oryza sativa subsp. japonica | Q6ETS8 |
| Arabidopsis thaliana | Q8LB37 |
| Encephalitozoon cuniculi | Q8SRR7 |
| Hevea brasiliensis | Q944G0 |
| Methanosarcina mazei | AAM31457.1 |
| Methanocaldococcus jannaschii | AAB98390.1 |
| Staphylococcus saprophyticus | BAE19266.1 |
| Streptococcus agalactiae | EAO73731.1 |
| Enterococcus faecalis | AAO80711.1 |
| Flavobacterium johnsoniae | ABQ04421.1 |
| Bdellovibrio bacteriovorus | CAE79505.1 |
| Chloroflexus aurantiacus | A9WEU8.1 |
| Legionella pneumophila | CAH13175.1 |
| Listeria monocytogenes | EAL09343.1 |
| Metallosphaera sedula | ABP95731.1 |
| Staphylococcus epidermidis | AAO03959.1 |
| Streptococcus thermophilus | AAV60266.1 |
| Bacillus coagulans | EAY45229.1 |
| Chloroflexus aggregans | EAV09355.1 |
| Lactobacillus brevis | ABJ64001.1 |
| Lactobacillus fermentum | BAG27529.1 |
| Lactobacillus plantarum | CAD64155.1 |
| Lactobacillus salivarius | ABD99494.1 |
| Lactococcus lactis sp. lactis | AAK04503.1 |
| Dichelobacter nodosus | ABQ14154.1 |
| Flavobacterium psychrophilum | CAL42423.1 |
| Streptococcus pneumoniae | EDT95457.1 |
| Streptococcus pyogenes | AAT86835.1 |
| Streptococcus suis | ABP91444.1 |
| Staphylococcus haemolyticus | BAE05710.1 |
| Streptococcus equi | ACG62435.1 |
| Arabidopsis thaliana | AAC67348.1 |
| Borrelia afzelii | ABH01961.1 |
| Encephalitozoon cuniculi | CAD25409.1 |
| Streptomyces sp. | BAB07791.1 |
| Streptococcus agalactiae | EAO73731.1 |
| Streptococcus uberis | CAR41735.1 |
| Gallus gallus | XP_423130 |
| Salmo salmar | ACI34234 |
| Natromonas pharaonis | CAI48881.1 |
| Haloarcula marismortui | AAV46412.1 |
| Haloquadratum walsbyi | CAJ51653.1 |

In a preferred embodiment the decarboxylase employed in the method according to the invention is a diphosphomevalonate decarboxylase from *Picrophilus torridus* or an organism which is evolutionary closely related to *Picrophilus torridus*. In a further preferred embodiment the decarboxylase originates from an organism of the genus *Picrophilus*, *Thermoplasma* or *Ferroplasma*, more preferably of the species *Picrophilus torridus* (GenBank accession number AAT43941; Swissprot/TrEMBL accession number Q6KZB1), *Picrophilus oshimae*, *Thermoplasma volcanicum* (GenBank accession number BAB59465; Swissprot/TrEMBL accession number Q97BY2), *Thermoplasma acidophilum* (GenBank accession number CAC12426; Swissprot/TrEMBL accession number Q9HIN1)), *Ferroplasma acidarmanus* fer1 (GenBank accession number ZP_05571615) or *Ferroplasma cupricumulans*.

In another preferred embodiment the diphosphomevalonate decarboxylase originates from an organism of the genus *Streptococcus*, *Homo* or *Lactobacillus*, preferably of the species *Streptococcus gordonii*, *Streptococcus infantarius*, *Streptococcus mitis*, *Streptococcus gallolyticus*, *Streptococcus sanguinis*, *Streptococcus* sp. M143, *Streptococcus suis* or *Streptococcus salivarius*. Even more preferably, the diphosphomevalonate decarboxylase is or is derived from the diphosphomevalonate decarboxylase of *Streptococcus gordonii* str. Challis substr. CH1 (GenBank accession number AAT43941; Swissprot/TrEMBL accession number A8UU9), of *Streptococcus infantarius* subsp *infantarius* ATCC BAA-102 (GenBank accession number EDT48420.1; Swissprot/TrEMBL accession number B1SCG0), of *Homo sapiens* (GenBank accession number AAC50440.1; Swissprot/TrEMBL accession number P53602.1), of *Lactobacillus delbrueckii* (GenBank accession number CAI97800.1; Swissprot/TrEMBL accession number Q1GAB2 of *Streptococcus mitis* (strain B6) (GenBank accession number CBJ22986.1), of *Streptococcus gallolyticus* UCN34 (GenBank accession number CBI13757.1 of *Streptococcus sanguinis* SK36 (GenBank accession number ABN43791.1), of *Streptococcus* sp. M143 (GenBank accession number EFA24040.1), of *Streptococcus suis* 89/1591 (GenBank accession number EEF63672.1) or of *Streptococcus salivarius* SK126 (GenBank accession number EEK09252).

If a diphosphomevalonate decarboxylase is employed in the conversion of a 3-sulfonyloxy-1-carboxylic acid into the corresponding alkene, the presence of ATP in the reaction is not absolutely mandatory but could be beneficial. It is assumed that ATP might have an effect on the folding of the protein by the binding of ATP to the ATP-binding site of the diphosphomevalonate decarboxylase. It is considered that not only ATP but also other similar compounds like dATP, ADP, AMP or other NTPs or dNTPs have this effect. Thus, in a preferred embodiment, the method according to the present invention is carried out with ATP, dATP, ADP, AMP or an NTP other than ATP or a dNTP as co-substrate.

In another embodiment of the method according to the invention, the conversion of the 3-sulfonyloxy-1-carboxylic acid into a corresponding alkene is achieved by the use of an enzyme which is classified as a mevalonate-5-monophosphate decarboxylase or is an enzyme which is derived from such an enzyme and which has the capacity to convert a 3-sulfonyloxy-1-carboxylic acid as defined herein above into a corresponding alkene.

In a further embodiment of the method according to the invention, the conversion of the 3-sulfonyloxy-1-carboxylic acid into a corresponding alkene is achieved by the use of an enzyme which is classified as a terpene synthase.

The terpene synthases constitute an enzyme family which comprises enzymes catalyzing the formation of numerous natural products always composed of carbon and hydrogen (terpenes) and sometimes also of oxygen or other elements (terpenoids). Terpenoids are structurally diverse and widely distributed molecules corresponding to well over 30000 defined natural compounds that have been identified from all kingdoms of life. In plants, the members of the terpene synthase family are responsible for the synthesis of the various terpene molecules from two isomeric 5-carbon precursor "building blocks", isoprenyl diphosphate and prenyl diphosphate, leading to 5-carbon isoprene, 10-carbon monoterpene, 15-carbon sesquiterpene and 20-carbon diterpenes" (Chen et al.; The Plant Journal 66 (2011), 212-229).

The ability of terpene synthases to convert a prenyl diphosphate containing substrate to diverse products during different reaction cycles is one of the most unique traits of this enzyme class. The common key step for the biosynthesis of all terpenes is the reaction of terpene synthase on corresponding diphosphate esters. The general mechanism of this enzyme class induces the removal of the diphosphate group and the generation of an intermediate with carbocation as the first step. In the various terpene synthases, such intermediates further rearrange to generate the high number of terpene skeletons observed in nature. In particular, the resulting cationic intermediate undergoes a series of cyclizations, hydride shifts or other rearrangements until the reaction is terminated by proton loss or the addition of a nucleophile, in particular water for forming terpenoid alcohols (Degenhardt et al., Phytochemistry 70 (2009), 1621-1637).

The different terpene synthases share various structural features. These include a highly conserved C-terminal domain, which contains their catalytic site and an aspartate-rich DDXXD motif essential for the divalent metal ion (typically Mg2+ or Mn2+) assisted substrate binding in these enzymes (Green et al. Journal of biological chemistry, 284, 13, 8661-8669). In principle, any known enzyme which can be classified as belonging to the EC 4.2.3 enzyme superfamily can be employed.

In one embodiment of the present invention an isoprene synthase (EC 4.2.3.27) is used for the conversion of a 3-sulfonyloxy-1-carboxylic acid as defined above into a corresponding alkene. Isoprene synthase is an enzyme which catalyzes the following reaction:

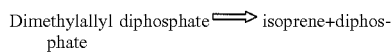
Dimethylallyl diphosphate ⇌ isoprene+diphosphate

This enzyme occurs in a number of organisms, in particular in plants and some bacteria. The occurrence of this enzyme has, e.g., been described for *Arabidopsis thaliana*, a number of *Populus* species like *P. alba* (UniProt accession numbers Q50L36, A9Q7C9, D8UY75 and D8UY76), *P. nigra* (UniProt accession number AOPFK2), *P. canescence* (UniProt accession number Q9AR86; see also Köksal et al., J. Mol. Biol. 402 (2010), 363-373), *P. tremuloides*, *P. trichocarpa*, in *Quercus petraea*, *Quercus robur*, *Salix discolour*, *Pueraria montana* (UniProt accession number Q6EJ97), *Pueraria montana* var. *lobata*, *Mucuna pruriens*, *Vitis vinifera*, *Embryophyta* and *Bacillus subtilis*. In principle, any known isoprene synthase can be employed in the method according to the invention. In a preferred embodiment, the isoprene synthase employed in a method according to the present invention is an isoprene synthase from a plant of the genus *Populus*, more preferably from *Populus trichocarpa* or *Populus alba*. In another preferred embodiment the isoprene synthase employed in a method according to the present invention is an isoprene synthase from *Pueraria montana*, preferably from *Pueraria montana* var. *lobata*, or from *Vitis vinifera*. Preferred isoprene synthases to be used in the context of the present invention are the isoprene synthase of *Populus alba* (Sasaki et al.; FEBS Letters 579 (2005), 2514-2518) or the isoprene synthases from *Populus trichocarpa* and *Populus tremuloides* which show very high sequence homology to the isoprene synthase from *Populus alba*. Another preferred isoprene synthase is the isoprene synthase from *Pueraria montana* var. *lobata* (kudzu) (Sharkey et al.; Plant Physiol. 137 (2005), 700-712).

The activity of an isoprene synthase can be measured according to methods known in the art, e.g. as described in Silver and Fall (Plant Physiol (1991) 97, 1588-1591). In a typical assay, the enzyme is incubated with dimethylallyl diphosphate in the presence of the required co-factors, $Mg^{2+}$ or $Mn^{2+}$ and $K^+$ in sealed vials. At appropriate time volatiles compound in the headspace are collected with a gas-tight syringe and analyzed for isoprene production by gas chromatography (GC).

Moreover, it is not only possible to use an isoprene synthase for converting a 3-sulfonyloxy-1-carboxylic acid into a corresponding alkene according to the method of the present invention, but it is also possible to use other enzymes from the family of monoterpene synthases. Monoterpene synthases comprise a number of families to which specific EC numbers are allocated. However, they also include also a number of enzymes which are simply referred to as monoterpene synthases and which are not classified into a specific EC number. To the latter group belong, e.g., the monoterpene synthases of *Eucalyptus globulus* (UniProt accession number Q0PCI4) and of *Melaleuca alternifolia* described in Shelton et al. (Plant Physiol. Biochem. 42 (2004), 875-882). In particularly preferred embodiments of the present invention use is made of a monoterpene synthase of *Eucalyptus globulus* or of *Melaleuca*.

In other preferred embodiments of the method according to the invention the conversion of a 3-sulfonyloxy-1-carboxylic acid into a corresponding alkene according to the above shown scheme is achieved by a terpene synthase belonging to one of the following families: alpha-farnesene synthases (EC 4.2.3.46), beta-farnesene synthases (EC 4.2.3.47), myrcene/(E)-beta-ocimene synthases (EC 4.2.3.15), pinene synthase (EC 4.2.3.14), limonene synthase (EC 4.2.3.16 and EC 4.2.3.20).

Farnesene synthases are generally classified into two different groups, i.e. alpha-farnesene synthases (EC 4.2.3.46) and beta farnesene synthases (EC 4.2.3.47). Alpha-farnesene synthases (EC 4.2.3.46) naturally catalyze the following reaction:

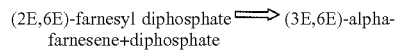
(2E,6E)-farnesyl diphosphate ⇌ (3E,6E)-alpha-farnesene+diphosphate

This enzyme occurs in a number of organisms, in particular in plants, for example in *Malus×domestica* (UniProt accession numbers Q84LB2, B2ZZ11, Q6Q2J2, Q6QWJ1 and Q32WI2), *Populus trichocarpa*, *Arabidopsis thaliana* (UniProt accession numbers A4FVP2 and POCJ43), *Cucumis melo* (UniProt accession number B2KSJ5) and *Actinidia deliciosa* (UniProt accession number C7SHN9). In principle, any known alpha-farnesene synthase can be employed in the method according to the invention. In a preferred embodiment, the alpha-farnesene synthase employed in a method according to the present invention is an alpha-farnesene synthase from *Malus×domestica* (e.g. UniProt accession numbers Q84LB2, B2ZZ11, Q6Q2J2, Q6QWJ1 and Q32WI2; see also Green et al.; Photochemistry 68 (2007), 176-188).

Beta-farnesene synthases (EC 4.2.3.47) naturally catalyze the following reaction:

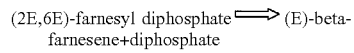
(2E,6E)-farnesyl diphosphate ⇌ (E)-beta-farnesene+diphosphate

This enzyme occurs in a number of organisms, in particular in plants and in bacteria, for example in *Artemisia annua* (UniProt accession number Q4VM12), *Citrus junos* (UniProt accession number Q94JS8), *Oryza sativa* (UniProt accession number Q0J7R9), *Pinus sylvestris* (UniProt accession number D7PCH9), *Zea diploperennis* (UniProt accession number C7E5V9), *Zea mays* (UniProt accession numbers Q2NM15, C7E5V8 and C7E5V7), *Zea perennis* (UniProt accession number C7E5W0) and *Streptococcus coelicolor* (Zhao et al., J. Biol. Chem. 284 (2009), 36711-36719). In principle, any known beta-farnesene synthase can be employed in the method according to the invention. In a preferred embodiment, the beta-farnesene synthase employed in a method according to the present invention is a beta-farnesene synthase from *Mentha piperita* (Crock et al.; Proc. Natl. Acad. Sci. USA 94 (1997), 12833-12838).

Methods for the determination of farnesene synthase activity are known in the art and are described, for example, in Green et al. (Phytochemistry 68 (2007), 176-188). In a typical assay farnesene synthase is added to an assay buffer containing 50 mM BisTrisPropane (BTP) (pH 7.5), 10% (v/v) glycerol, 5 mM DTT. Tritiated farnesyl diphosphate and metal ions are added. Assays containing the protein are overlaid with 0.5 ml pentane and incubated for 1 h at 30° C. with gentle shaking. Following addition of 20 mM EDTA (final concentration) to stop enzymatic activity an aliquot of the pentane is removed for scintillation analysis. The olefin products are also analyzed by GC-MS.

Myrcene/(E)-beta-ocimene synthases (EC 4.2.3.15) are enzymes which naturally catalyze the following reaction:

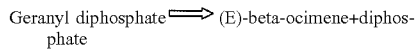

or

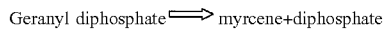

These enzymes occur in a number of organisms, in particular in plants and animals, for example in *Lotus japanicus* (Arimura et al.; Plant Physiol. 135 (2004), 1976-1983), *Phaseolus lunatus* (UniProt accession number B1P189), *Abies grandis, Arabidopsis thaliana* (UniProt accession number Q9ZUH4), *Actinidia chinensis, Vitis vinifera* (E5GAG5), *Perilla fructescens, Ochtodes secundiramea* and in *Ips pini* (UniProt accession number Q58GE8). In principle, any known myrcene/ocimene synthase can be employed in the method according to the invention. In a preferred embodiment, the myrcene/ocimene synthase employed in a method according to the present invention is an (E)-beta-ocimene synthase from *Vitis vinifera*.

The activity of an ocimene/myrcene synthase can be measured as described, for example, in Arimura et al. (Plant Physiology 135 (2004), 1976-1983). In a typical assay for determining the activity, the enzyme is placed in screw-capped glass test tube containing divalent metal ions, e.g. $Mg^{2+}$ and/or $Mn^{2+}$, and substrate, i.e. geranyl diphosphate. The aqueous layer is overlaid with pentane to trap volatile compounds. After incubation, the assay mixture is extracted with pentane a second time, both pentane fractions are pooled, concentrated and analyzed by gas chromatography to quantify ocimene/myrcene production.

Pinene synthase (EC 4.2.3.14) is an enzyme which naturally catalyzes the following reaction:

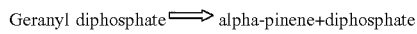

This enzyme occurs in a number of organisms, in particular in plants, for example in *Abies grandis* (UniProt accession number O244475), *Artemisia annua, Chamaecyparis formosensis* (UniProt accession number C3RSF5), *Salvia officinalis* and *Picea sitchensis* (UniProt accession number Q6XDB5).

For the enzyme from *Abies grandis* a particular reaction was also observed (Schwab et al., Arch. Biochem. Biophys. 392 (2001), 123-136), namely the following:

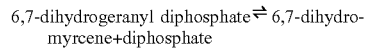

In principle, any known pinene synthase can be employed in the method according to the invention. In a preferred embodiment, the pinene synthase employed in a method according to the present invention is a pinene synthase from *Abies grandis* (UniProt accession number O244475; Schwab et al., Arch. Biochem. Biophys. 392 (2001), 123-136).

Methods for the determination of pinene synthase activity are known in the art and are described, for example, in Schwab et al. (Archives of Biochemistry and Biophysics 392 (2001), 123-136). In a typical assay, the assay mixture for pinene synthase consists of 2 ml assay buffer (50 mM Tris/HCl, pH 7.5, 500 mM KCl, 1 mM MnCl2, 5 mM dithiothreitol, 0.05% NaHSO3, and 10% glycerol) containing 1 mg of the purified protein. The reaction is initiated in a Teflon-sealed screw-capped vial by the addition of 300 mM substrate. Following incubation at 25° C. for variable periods (0.5-24 h), the mixture is extracted with 1 ml of diethyl ether. The biphasic mixture is vigorously mixed and then centrifuged to separate the phases. The organic extract is dried (MgSO4) and subjected to GC-MS and MDGC analysis.

Limonene synthase (EC 4.2.3.16) is an enzyme which naturally catalyzes the following reaction:

This enzyme occurs in a number of organisms, in particular in plants, for example in *Cannabis sativa, Abies grandis, Picea abies* (UniProt accession number Q675L1), *Picea sitchensis* UniProt accession number Q20HU7), *Mentha* sp., *Mentha spicata, Mentha×piperita, Perilla frutescens*, in *Ricciocarpos natans* and in *Agastache rugosa*.

Limonene synthase (EC 4.2.3.20) is an enzyme which naturally catalyzes the following reaction:

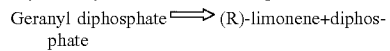

This enzyme occurs in a number of organisms, in particular in plants, for example in *Lavandula angustifolia* (UniProt accession number Q2XSC6), *Schizonepeta tenuifolia* (UniProt accession number Q9FUW5), *Perilla frutescens, Citrus limon* (UniProt accession numbers Q8L5K1 and Q8L5K3), *Citrus unshiu* (UniProt accession number Q6F5H2), *Carum carvi* and *Schizonepeta tenuifolia*.

In principle, any known limonene synthase can be employed in the method according to the invention. Methods for the determination of limonene synthase activity are known in the art and are described, for example, in Maruyama et al. (Biol. Pharm. Bull. 24 (2001), 373-377). Such a method comprises, e.g., that the enzyme is incubated with 50 mM geranyl diphosphate in 500 μl of 25 mM potassium phosphate buffer pH 7.6, containing 1 mM 1,4-dithiothreitol and 15 mM $MgCl_2$ for 12 hours at 31° C. The incubation mixture is overlaid with 500 μl diethyl ether to trap volatile products. After incubation the reaction mixture is extracted with 500 μl of diethyl ether twice and the combined extract is dried on $MgSO_4$ and then analyzed by GC-MS.

In a further embodiment of the method according to the invention, the conversion of the 3-sulfonyloxy-1-carboxylic acid into a corresponding alkene is achieved by the use of an enzyme which is classified as a retinol sulfotransferase/ dehydratase. This enzyme has been described above in connection with the description of the first step of the method according to the present invention and the same as described above also applies here.

In a further embodiment of the method according to the invention, the conversion of the 3-sulfonyloxy-1-carboxylic acid into a corresponding alkene is achieved by the use of an enzyme which is classified as a thioesterase, more preferably a CurM thioesterase (in the following referred to as PKS thioesterase (TE)) or a thioesterase from the olefin synthase (OLS) from the hydrocarbon-producing system of *Synechococcus* PCC 7002 (in the following referred to as the OLS thioesterase (TE)). The CurM protein is part of the polyketide synthase (PKS) which is involved in the synthesis of curacin A, a natural product with potent anticancer properties generated by the marine *cyanobacterium* Lyngbya majuscule. CurM itself has an unusual structure with a C-terminal tridomain composed of an acyl carrier protein (ACP), a sulfotransferase (ST) and a thioesterase (TE). The PKS TE, its structure and its mechanism of action have been studied in detail and are described, e.g., in Gu et al. (J. AM. Chem. Soc. 131 (2009), 16033-16035) and Gehret et al. (J. Biol. Chem. 286 (2011), 14445-14454). Similarly, the thioesterase (TE) domain of the olefin synthase (OLS) from the hydrocarbon-producing system of *Synechococcus* PCC 7002 is also part of a tridomain containing an acyl carrier protein (ACP), a sulfotransferase (ST) and the thioesterase (TE). The PKS and OLS thioesterases act on sulfated substrates to hydrolyze, decarboxylate and eliminate sulfate to yield a terminal alkene product in their natural reactions.

Figure 4:
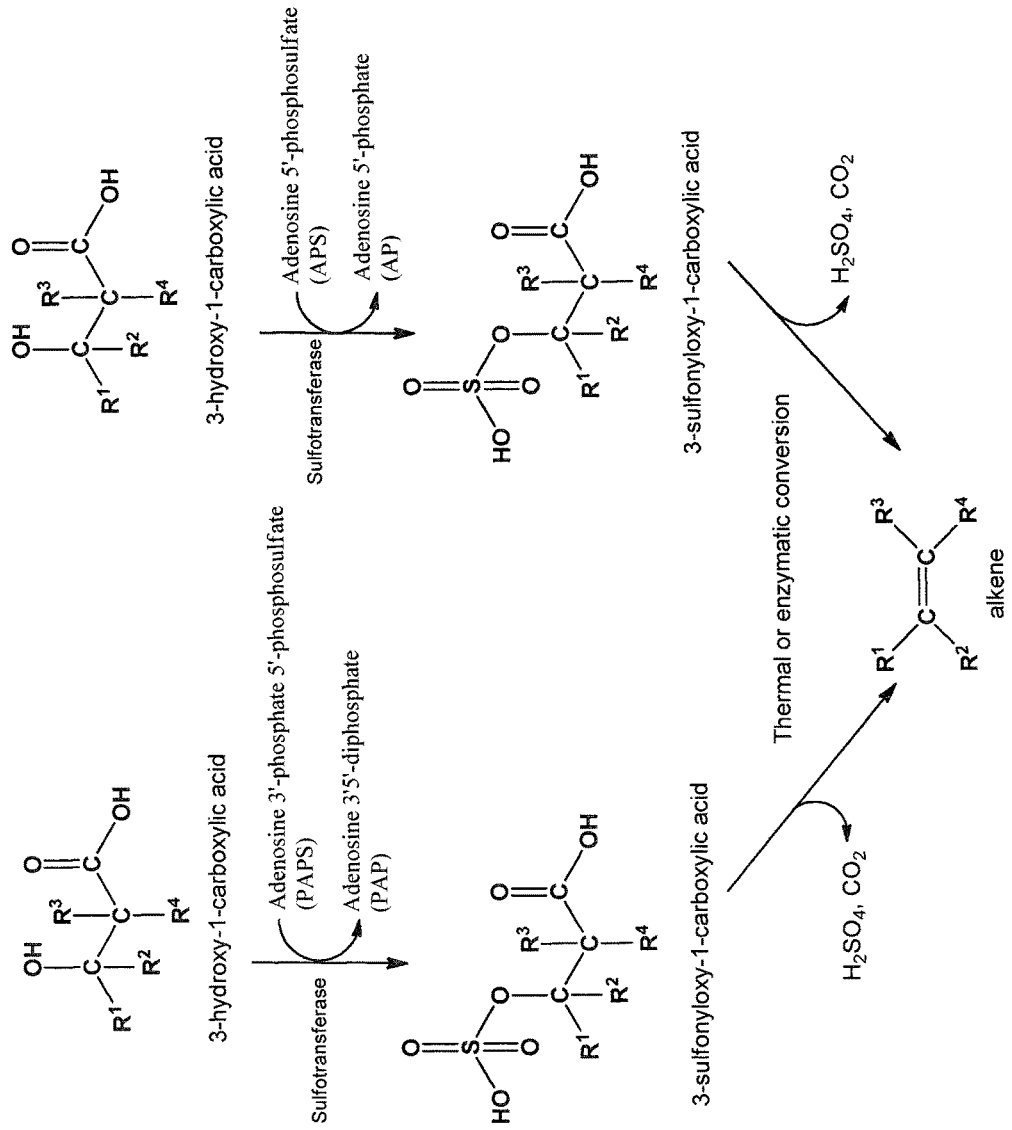

In a preferred embodiment, the TE employed in the method according to the present invention is a PKS (TE) protein having the sequence as shown in FIG. 4 of Gehret et al. (J. Biol. Chem. 286 (2011), 14445-14454) or as available in Uniprot accession number DOE8E2 (residues 1929 to 2211) or an OLS (TE) protein having the sequence as in Uniprot accession number B1XKC6 (residues 2435 to 2720).

However, it is not only possible to use in a method according to the present invention the TE domains of the two above mentioned specific enzymes PKS or OLS but also thioesterases which are highly homologous to these TE domains, e.g. which show more than 50%, preferably more than 70%, even more preferably more than 80%, particularly preferred more than 90% sequence identity and which show the same enzymatic activity. Accordingly, the term PKS or OLS thioesterase (TE) also means enzymes which show the above mentioned sequence identity and the same enzymatic activity.

An enzyme employed in the process according to the invention can be a naturally occurring enzyme or it can be an enzyme which is derived from a naturally occurring enzyme, e.g. by the introduction of mutations or other alterations which, e.g., alter or improve the enzymatic activity, the stability, etc.

When the present invention refers to a sulfotransferase to be used for the conversion of a 3-hydroxy-1-carboxylic acid into a 3-sulfonyloxy-1-carboxylic acid as described above, such reference to a sulfotransferase also covers enzymes which are derived from such a sulfotransferase, which are capable of catalyzing the conversion of a 3-hydroxy-1-carboxylic acid into a 3-sulfonyloxy-1-carboxylic acid as described above but which only have a low affinity to their natural substrate or do no longer accept their natural substrate.

When the present invention refers to a certain enzyme to be used for the conversion of a 3-sulfonyloxy-1-carboxylic acid into the corresponding alkene as described above, such reference to an enzyme also covers enzymes which are derived from such an enzyme, which are capable of catalyzing the conversion of a 3-sulfonyloxy-1-carboxylic acid into the corresponding alkene as described above but which only have a low affinity to their natural substrate or do no longer accept their natural substrate.

Such a modification of the preferred substrate of an enzyme to be employed in a method according to the present invention allows to improve the conversion of the respective substrate of a reaction of a method according to the present invention and to reduce the production of unwanted by-product(s) due to the action of the enzyme on their natural substrate(s). Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic engineering in prokaryotic cells, a nucleic acid molecule encoding an enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for their enzymatic activity and in particular for their capacity to convert a substrate as indicated in the respective reaction of a method according to the invention as a substrate rather than their natural substrate(s) as described above in connection with the description of the different enzymes which can be used in the context of the methods according to the present invention. Assays for measuring the capacity of an enzyme to catalyze a reaction as indicated in connection with a Pathway of a method according to the invention are described in the Examples.

The modified version of the enzyme having a low affinity to its natural substrate or no longer accepting its natural substrate may be derived from a naturally occurring enzyme or from an already modified, optimized or synthetically produced enzyme.

An enzyme employed in the process according to the present invention can be a natural version of the protein or a synthetic protein as well as a protein which has been chemically synthesized or produced in a biological system or by recombinant processes. The enzyme may also be chemically modified, for example in order to improve its/their stability, resistance, e.g. to temperature, for facilitating its purification or its immobilization on a support. The enzyme may be used in isolated form, purified form, in immobilized form, as a crude or partially purified extract obtained from cells synthesizing the enzyme, as chemically synthesized enzyme, as recombinantly produced enzyme, in the form of microorganisms producing them etc. The enzyme used in the invention can thus be natural or synthetic, and produced by chemical, biological or genetic means. It can also be chemically modified, for example in order to improve its activity, resistance, specificity, purification, or to immobilize it on a support.

The methods according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form. In another embodiment the enzymes employed in the method are present in the reaction as a non-purified extract, or else in the form of non-lysed bacteria, so as to economize on protein purification costs.

For carrying out the process in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the corresponding alkene. The production of the alkene can be measured by methods known in the art, such as gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

The in vitro method according to the invention may be carried out in a one-pot-reaction, i.e. the substrate is combined in one reaction mixture with the above described enzymes necessary for the conversion into the corresponding alkene and the reaction is allowed to proceed for a time sufficient to produce the alkene. Alternatively, the method may also be carried out by effecting the different steps in a consecutive manner, i.e. by first mixing the 3-hydroxy-1-carboxylic acid with one or more enzymes and allowing the reaction to proceed to the 3-sulfonyloxy-1-carboxylic acid and then either increasing the temperature so as to achieve a thermal conversion of the 3-sulfonyloxy-1-carboxylic acid into the corresponding alkene or by adding one or more further enzymes to convert the 3-sulfonyloxy-1-carboxylic acid further either into the corresponding alkene.

The recovery of the produced alkene may involve one step or multiples steps. For example, the alkene can be recovered using standard techniques such as adsorption/desorption, gas stripping, fractionation. Separation of the produced alkene from $CO_2$ can be achieved by the condensation of $CO_2$ at low temperature. $CO_2$ can also be removed by polar solvents, e.g. ethanolamine.

In another embodiment the method according to the invention is carried out in vivo. Thus, in another embodiment the method may be carried out in culture, in the presence of an organism, preferably a microorganism, producing an enzyme described above which can convert a 3-hydroxy-1-carboxylic acid into a 3-sulfonyloxy-1-carboxylic acid and which optionally also produces an enzyme necessary for further converting the 3-sulfonyloxy-1-carboxylic acid into the corresponding alkene as described herein above. Such organisms or microorganisms are also an object of the present invention.

If a (micro)organism is used which naturally expresses one of the required enzyme activities, it is possible to modify such a (micro)organism so that this activity is overexpressed in the (micro)organism. This can, e.g., be achieved by effecting mutations in the promoter region of the corresponding gene so as to lead to a promoter which ensures a higher expression of the gene. Alternatively, it is also possible to mutate the gene as such so as to lead to an enzyme showing a higher activity. By using (micro)organisms which express the enzymes which are necessary to convert a 3-hydroxy-1-carboxylic acid into a 3-sulfonyloxy-1-carboxylic acid and which optionally also produce an enzyme necessary for further converting the 3-sulfonyloxy-1-carboxylic acid into the corresponding alkene as described herein above, it is possible to carry out the method according to the invention directly in the culture medium, without the need to separate or purify the enzymes.

In one embodiment the (micro)organism according to the present invention or employed in the method according to the invention is an organism, preferably a microorganism, which has been genetically modified to contain one or more foreign nucleic acid molecules encoding one or more of the enzymes as described above in connection with the conversion of a 3-hydroxy-1-carboxylic acid into a 3-sulfonyloxy-1-carboxylic acid and which optionally also produces an enzyme necessary for further converting the 3-sulfonyloxy-1-carboxylic acid into the corresponding alkene as described herein above. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular in microorganisms, are well known to the person skilled in the art.

In a further embodiment the nucleic acid molecule is foreign to the organism/microorganism in that the encoded enzyme is not endogenous to the organism/microorganism, i.e. is naturally not expressed by the organism/microorganism when it is not genetically modified. In other words, the encoded enzyme is heterologous with respect to the organism/microorganism. The foreign nucleic acid molecule may be present in the organism/microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The organisms used in the invention can be prokaryotes or eukaryotes, preferably, they are microorganisms such as bacteria, yeasts, fungi or molds, or plant cells or animal cells. In a particular embodiment, the microorganisms are bacteria, preferably of the genus *Escherichia*, *Alcaligenes* or *Bacillus* and even more preferably of the species *Escherichia coli*, *Alcaligenes eutrophus* or *Bacillus megaterium*.

In a further preferred embodiment the microorganism is a fungus, more preferably a fungus of the genus *Saccharomyces, Schizosaccharomyces, Aspergillus, Pichia, Trichoderma* or *Kluyveromyces* and even more preferably of the species *Saccharomyces cerevisiae, Schizosaccharomyces pombe, Aspergillus niger, Trichoderma reesei, Pichia pastoris* or of the species *Kluyveromyces lactis*.

In another preferred embodiment, the method according to the invention makes use of a photosynthetic microorganism expressing an enzyme which is capable of catalyzing the conversion of a 3-hydroxy-1-carboxylic acid into a 3-sulfonyloxy-1-carboxylic acid and which optionally also produces an enzyme which can catalyze the conversion of the 3-sulfonyloxy-1-carboxylic acid into the corresponding alkene as described herein above. Preferably, the microorganism is a photosynthetic bacterium or a microalgae. In a further embodiment the microorganism is an algae, more preferably an algae belonging to the diatomeae.

It is also conceivable to use in the method according to the invention one microorganism that produces an enzyme catalyzing the conversion of a 3-hydroxy-1-carboxylic acid into a 3-sulfonyloxy-1-carboxylic acid as described above and another microorganism that produces an enzyme catalyzing the conversion of the 3-sulfonyloxy-1-carboxylic acid into the corresponding alkene as described above.

In another preferred embodiment the method according to the invention makes use of a multicellular organism expressing an enzyme which can catalyze the conversion of a 3-hydroxy-1-carboxylic acid into a 3-sulfonyloxy-1-carboxylic acid and which optionally also produces an enzyme which can catalyze the conversion of the 3-sulfonyloxy-1-carboxylic acid into the corresponding alkene as described herein above. Examples for such organisms are plants or animals.

The present invention also relates to the (micro)organism as described hereinabove in connection with the method according to the invention.

In a particularly preferred embodiment, the method involves culturing microorganisms in standard culture conditions (30-37° C. at 1 atm, in a fermenter allowing aerobic growth of the bacteria) or non-standard conditions (higher temperature to correspond to the culture conditions of thermophilic organisms, for example).

In one particularly preferred embodiment the method according to the present invention employs an organism, preferably a microorganism, which is mesophilic and which can be cultured at temperatures of around 30° C. to 37° C. For those 3-sulfonyloxy-1-carboxylic acids which can be thermally converted into the corresponding alkene at such temperatures, the (micro)organism only needs to express an enzyme necessary for the conversion of a 3-hydroxy-1-carboxylic acid into a 3-sulfonyloxy-1-carboxylic acid as described above and the conversion of the 3-sulfonyloxy-1-carboxylic acid into the corresponding alkene as described above is then achieved by thermal conversion.

In another particularly preferred embodiment the method according to the present invention employs an organism, preferably a microorganism, which is thermophilic and which can be cultured at higher temperatures, e.g. higher than 60° C. In such a case the (micro)organism only needs to express an enzyme necessary for the conversion of a 3-hydroxy-1-carboxylic acid into a 3-sulfonyloxy-1-carboxylic acid as described above and the conversion of the 3-sulfonyloxy-1-carboxylic acid into the corresponding alkene as described above is achieved by thermal conversion.

In a further embodiment the method of the invention is carried out under conditions under which the produced alkene is in a gaseous state. In such a case, it is furthermore preferred that the method is carried out under microaerophilic conditions. This means that the quantity of injected air is limiting so as to minimize residual oxygen concentrations in the gaseous effluents containing the alkene.

In another embodiment the method according to the invention furthermore comprises the step of collecting the gaseous alkene degassing out of the reaction. Thus in a preferred embodiment, the method is carried out in the presence of a system for collecting the alkene under gaseous form during the reaction.

As a matter of fact, short alkenes, and particularly ethylene, propylene and butene isomers, adopt the gaseous state at room temperature and atmospheric pressure. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

In a particular embodiment, the method also comprises detecting the alkene (for example propylene, ethylene or isobutylene) which is present in the gaseous phase. The presence of the compound to be produced in an environment of air or another gas, even in small amounts, can be detected by using various techniques and in particular by using gas chromatography systems with infrared or flame ionization detection, or by coupling with mass spectrometry.

In a particular embodiment, the alkenes produced by a method according to the invention are condensed, then optionally reduced, by using techniques known to one of skill in the art, so as to produce longer chain alkenes, or longer chain alkanes. For example, isobutylene can be used to synthesize isooctane: the catalytic methods for successfully carrying out this reaction have already been fully described.

In another embodiment the organism employed in the method according to the invention is a plant. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, wheat, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as *eucalyptus*, poplar or rubber tree (*Hevea brasiliensis*).

When the process according to the invention is carried out in vivo by using an organism/microorganism providing the respective enzyme activities, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

The present invention also relates to organisms, preferably microorganisms, which produce the enzymes necessary for the conversion of a 3-hydroxy-1-carboxylic acid into a 3-sulfonyloxy-1-carboxylic acid and for further converting the 3-sulfonyloxy-1-carboxylic acid into the corresponding alkene as described herein above. Thus, the present invention, in particular, relates to a (micro)organism which expresses
(a) a sulfotransferase; and
(b) a terpene synthase or a diphosphomevalonate decarboxylase or a mevalonate-5-monophosphate decarboxylase or a retinol sulfotransferase/dehydratase or a PKS or OLS thioesterase.

In a preferred embodiment the sulfotransferase according to (a) and (b) are different from each other.

The present invention also relates to a composition comprising an organism as defined above and a 3-hydroxy-1-carboxylic acid according to formula I.

As regards the preferred embodiments of the enzymes to be expressed in such a microorganism, the same applies as has been set forth above in connection with the method according to the present invention. In a preferred embodiment such an organism is a recombinant organism in the sense that it is genetically modified due to the introduction of at least one nucleic acid molecule encoding at least one of the above mentioned enzymes. Preferably such a nucleic acid molecule is heterologous with regard to the organism which means that it does not naturally occur in said organism.

Thus, the present invention also relates to an organism, preferably a microorganism, comprising a nucleic acid molecule coding for an enzyme as defined in (a) above and comprising a nucleic acid molecule coding for an enzyme as defined in (b) above. In a preferred embodiment at least one of the nucleic acid molecules is heterologous to the organism which means that it does not naturally occur in said organism. The microorganism is preferably a bacterium, a yeast or a fungus. In another preferred embodiment the organism is a plant or non-human animal. As regards other preferred embodiments, the same applies as has been set forth above in connection with the method according to the invention.

Moreover, the present invention also relates to a composition comprising a microorganism according to the present invention, a suitable culture medium and a 3-hydroxy-1-carboxylic acid or a carbon source that can be converted by the microorganism to a 3-hydroxy-1-carboxylic acid.

The present invention also relates to a composition comprising a sulfotransferase and a 3-hydroxy-1-carboxylic acid of formula I.

The present invention also relates to a composition comprising
(a) a terpene synthase or a diphosphomevalonate decarboxylase or a mevalonate-5-monophosphate decarboxylase or a retinol sulfotransferase/dehydratase or a PKS or OLS thioesterase; and
(b) a 3-sulfonyloxy-1-carboxylic acid of formula II.

Moreover, the present invention also relates to a composition comprising
(a) a sulfotransferase; and
(b) a terpene synthase or a diphosphomevalonate decarboxylase or a mevalonate-5-monophosphate decarboxylase or a retinol sulfotransferase/dehydratase or a PKS or OLS thioesterase.

In a preferred embodiment such a composition also comprises a 3-hydroxy-1-carboxylic acid of formula I. In another preferred embodiment the compositions comprises two different sulfotransferases, i.e. the sulfotransferases mentioned in (a) and (b), respectively, are different from each other.

The present invention also relates to the use of a sulfotransferase for the conversion of a 3-hydroxy-1-carboxylic acid of formula I into a 3-sulfonyloxy-1-carboxylic acid of formula II as described herein above.

Furthermore, the present invention relates to the use of a terpene synthase or a diphosphomevalonate decarboxylase or a mevalonate-5-monophosphate decarboxylase or a retinol sulfotransferase/dehydratase or a PKS or OLS thioesterase for the conversion of a 3-sulfonyloxy-1-carboxylic acid of formula II into an alkene of formula III as described herein above.

The present invention also relates to the use of a combination comprising
(a) a sulfotransferase; and
(b) a terpene synthase or a diphosphomevalonate decarboxylase or a mevalonate-5-monophosphate decarboxylase or a retinol sulfotransferase/dehydratase or a PKS or OLS thioesterase
for the conversion of a 3-hydroxy-1-carboxylic acid of formula I into an alkene of formula III as described herein above.

As regards the preferred embodiments of the different components recited, the same applies as has been set forth above in connection with the method according to the invention.

Each publication, patent, patent application or other document cited in this application is hereby incorporated by reference in its entirety for all purposes to the same extent as if each were individually indicated to be incorporated.

Other aspects and advantages of the invention will be described in the following examples, which are given for purposes of illustration and not by way of limitation.

FIG. 1: shows the general reaction scheme for converting a 3-hydroxy-1-carboxylic acid into a 3-sulfonyloxy-1-carboxylic acid by employing a sulfotransferase and PAPS or APS as a co-factor.

FIG. 2: shows the conversion of the 3-sulfonyloxy-1-carboxylic acid into a corresponding alkene by a thermal conversion.

FIG. 3: shows the conversion of the 3-sulfonyloxy-1-carboxylic acid into a corresponding alkene by an enzymatic conversion.

FIG. 4: shows the general reaction scheme for converting a 3-hydroxy-1-carboxylic acid into a 3-sulfonyloxy-1-carboxylic acid and further into a corresponding alkene.

Figure 5:
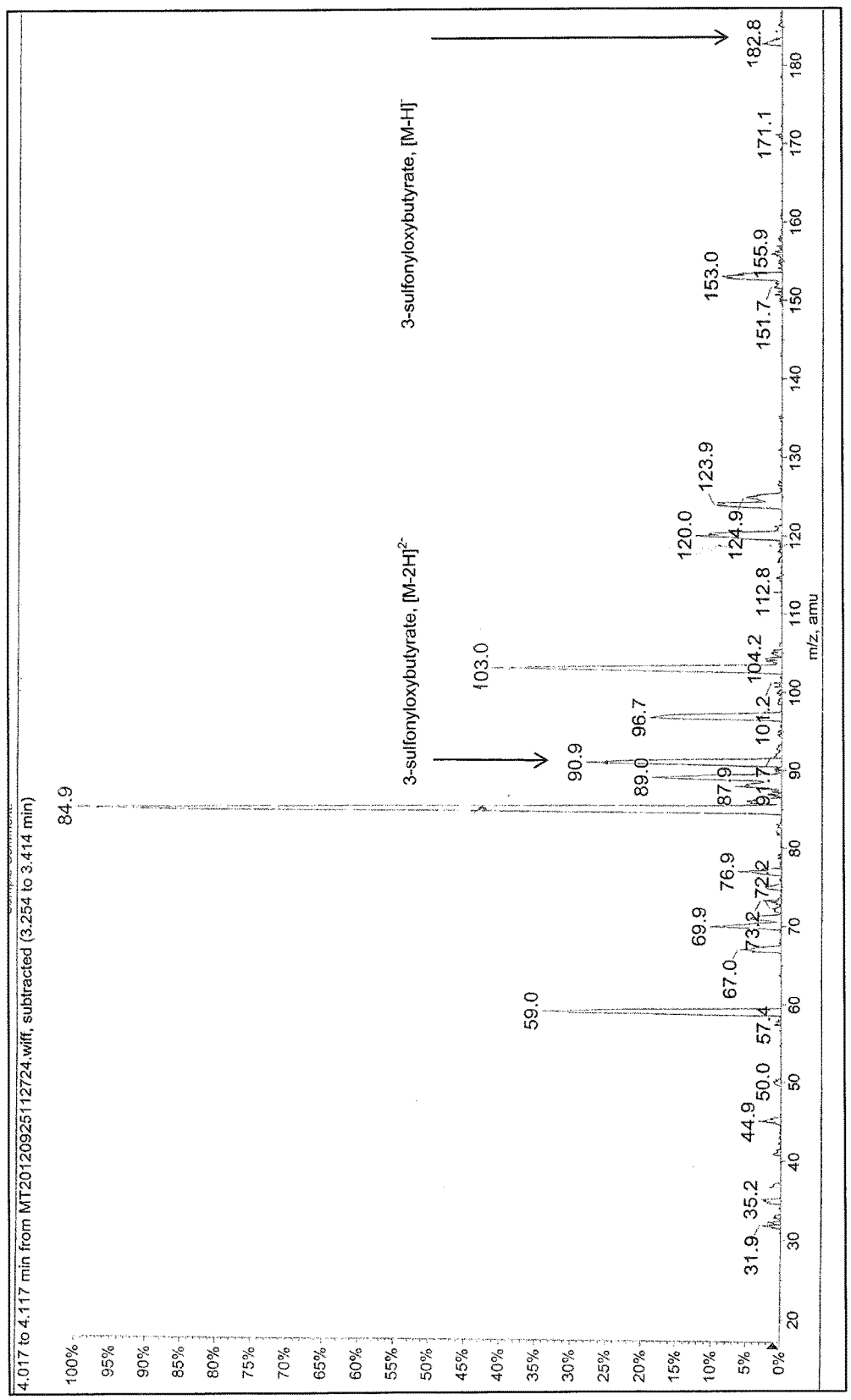

FIG. 5: shows Electrospray MS spectrum of sulfurylation reaction of 3-hydroxybutyrate using sulfotransferase CurM (PKS ST) from *Moorea producens* (formerly *Lyngbya majuscala*) 19L.

Figure 6:
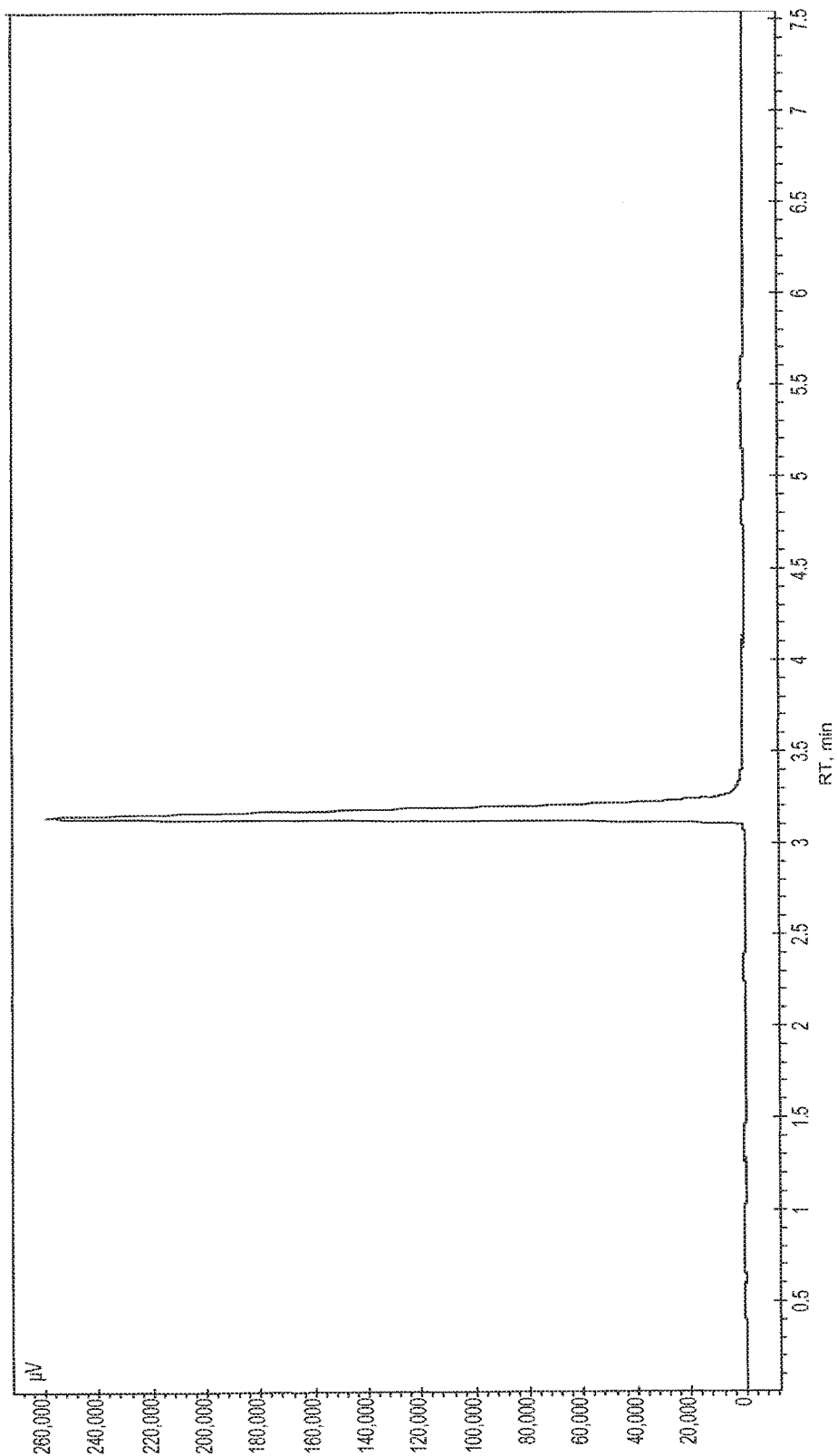

FIG. 6: shows GC analysis of assay of propylene production from disodium (R,S)-3-sulfonyloxybutyrate after 24 hours incubation at 37° C.

Figure 7:
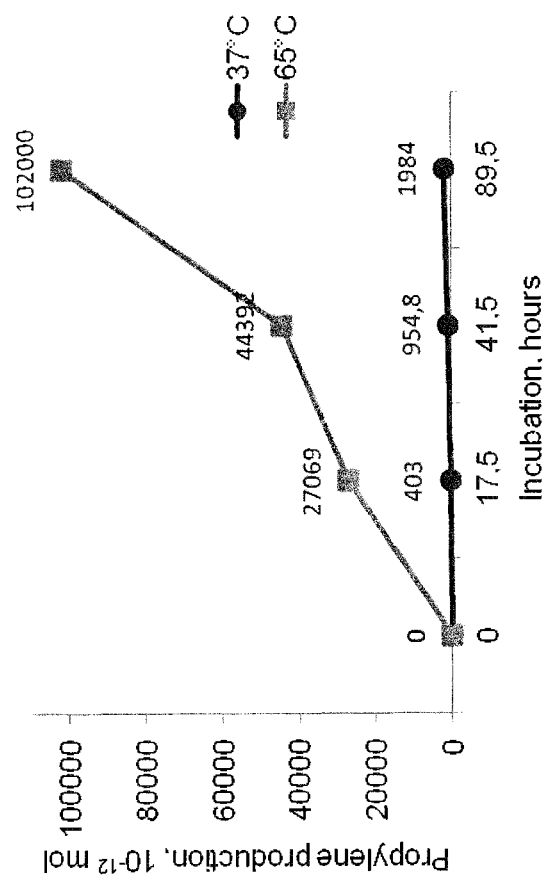

FIG. 7: shows Time courses study of propylene production from disodium (R,S)-3-sulfonyloxybutyrate at 37° C. and 65° C.

The following Examples serve to illustrate the invention.

EXAMPLES

Example 1: Cloning, Expression and Purification of Enzymes

Cloning and Bacterial Culture

The genes encoding the enzymes of interest were cloned in the pET 25b (+) vector. (Novagen). A stretch of 6 histidine codons was inserted after the methionine initiation codon to provide an affinity tag for purification. Competent *E. coli* BL21(DE3) cells (Novagen) were transformed with this vector according to the heat shock procedure. The transformed cells were grown with shaking (160 rpm) on ZYM-5052 auto-induction medium (Studier F W, *Prot. Exp. Pur.* 41, (2005), 207-234) for 6 hours at 37° C. and protein expression was continued at 18° C. overnight (approximately 16 hours). The cells were collected by centrifugation at 4° C., 10,000 rpm for 20 min and the pellets were frozen at −80° C.

Protein Purification and Concentration

The pellets from 200 ml of culture cells were thawed on ice and resuspended in 5 ml of $Na_2HPO_4$ pH 8 containing 300 mM NaCl, 5 mM $MgCl_2$ and 1 mM DTT. Twenty microliters of lysonase (Novagen) were added. Cells were incubated 10 minutes at room temperature and then returned to ice for 20 minutes. Cell lysis was completed by sonication for 3×15 seconds. The bacterial extracts were then clarified by centrifugation at 4° C., 10,000 rpm for 20 min. The clarified bacterial lysates were loaded on PROTINO-1000 Ni-TED column (Macherey-Nagel) allowing adsorption of 6-His tagged proteins. Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated and desalted on Amicon Ultra-4 10 kDa filter unit (Millipore) and resuspended in 0.25 ml 50 mM Tris-HCl pH 7.5 containing 0.5 mM DTT and 5 mM $MgCl_2$. Protein concentrations were quantified by direct UV 280 nm measurement on the NanoDrop 1000 spectrophotometer (Thermo Scientific). The purity of proteins varied from 70% to 90%.

Example 2: Mass Spectrometry Analysis of the 3-hydroxy-1-carboxylic acid Sulfurylation Reaction Using PAPS as Co-Substrate The enzymatic reactions were carried out under the following conditions:
50 mM Tris-HCl pH 7.5
5 mM DTT
100 mM NaCl
5-50 mM PAPS
5-100 mM 3-hydroxy-1-carboxylic acid
1-5 mg/ml purified sulfotransferase The reactions are initiated with the addition of purified sulfotransferase and incubated at 37° C. Control assays are performed in which either no enzyme is added, or no co-factor is added. Following incubation the samples are processed by mass spectrometry analysis. An aliquot of 50-200 µl reaction is removed, centrifuged and the supernatant is transferred to a clean vial. MS analyses are performed on a PE SCIEX API 2000 quadrupole mass spectrometer equipped with an electrospray ionization (ESI) source.

Example 3: Mass Spectrometry Analysis of the 3-hydroxy-1-carboxylic acid Sulfurylation Reaction Using APS as Co-Substrate The enzymatic reactions were carried out under the following conditions:
50 mM Tris-HCl pH 7.5
5 mM DTT
100 mM NaCl
5-50 mM APS
5-100 mM 3-hydroxy-1-carboxylic acid
1-5 mg/ml purified sulfotransferase The reactions are initiated with the addition of purified sulfotransferase and incubated at 37° C. Control assays are performed in which either no enzyme is added, or no co-factor is added. Following incubation the samples are processed by mass spectrometry analysis. An aliquot of 50-200 µl reaction is removed, centrifuged and the supernatant is transferred to a clean vial. MS analyses are performed on a PE SCIEX API 2000 quadrupole mass spectrometer equipped with an electrospray ionization (ESI) source.

Example 4: Mass Spectrometry Analysis of the 3-hydroxybutyrate sulfurylation Reaction Sequence of sulfotransferase domain of polyketide synthase CurM (PKS ST) inferred from the genome of *Moorea producens* (formerly *Lyngbya majuscala*) 19L was generated by oligonucleotide concatenation to fit the codon usage of *E. coli*. A stretch of 6 histidine codons was inserted after the methionine initiation codon to provide an affinity tag for purification. The gene thus synthesized was cloned in a pET25b(+) expression vector (the vectors were constructed by GENEART AG). After transformation of the *E. coli* strain BL21 (DE3), the protein was produced according to the procedure described in Example 1 and sulfotransferase activity was assayed under the following conditions
50 mM Tris-HCl pH 7.5
5 mM DTT
100 mM NaCl
5 mM PAPS
5 mM (R,S)-3-hydroxybutyrate
5 mg/ml purified sulfotransferase (ST) CurM.

Control reaction was performed using the same reaction mixture without addition of the enzyme. The assays were incubated for 1.5 hours at 37° C. An aliquot of 200 µl of each assay was then removed, filtered through a 0.45 µm filter and the filtrated solution was transferred into a clean vial. MS analyses were performed in negative electrospray mode by direct injection of sample using PE SCIEX API 2000 quadrupole instrument. The presence of 3-sulfonyloxybutyrate was evaluated. Mass spectra of enzymatic reaction showed characteristic peaks at m/z values of 182.8 and 90.9 (FIG. 5). The peak at m/z=182.8 was assigned to mono-deprotonated form of 3-sulfonyloxybutyrate, $[M-H]^-$. The peak at m/z=90.9 corresponds to double charged anion $[M-2H]^{2-}$ of 3-sulfonyloxybutyrate. No characteristic peak was observed in control reaction without enzyme.

Thus, the sulfotransferase CurM (PKS sulfotransferase ST) catalyzes transfer of the sulfate group from PAPS onto hydroxyl group of 3-hydroxybutyrate.

Example 5: Mass Spectrometry Analysis of the 3-hydroxy-3-methylbutyrate Sulfurylation Reaction Using PAPS as Co-Substrate The enzymatic reactions were carried out under the following conditions:
50 mM Tris-HCl pH 7.5
5 mM DTT
100 mM NaCl
5-50 mM PAPS
5-50 mM 3-hydroxy-3-methylbutyrate
1-5 mg/ml purified sulfotransferase The reactions are initiated with the addition of sulfotransferase and incubated at 37° C. Control assays are performed in which either no enzyme is added, or no co-factor is added. Following incubation the samples are processed by mass spectrometry analysis. An aliquot of 50-200 µl reaction is removed, centrifuged and the supernatant is transferred to a clean vial. MS analyses are performed on a PE SCIEX API 2000 quadrupole mass spectrometer equipped with an electrospray ionization (ESI) source.

Example 6: Thermal Conversion of 3-sulfonyloxy-1-carboxylic acids to Corresponding Alkenes Thermal conversion of 3-sulfonyloxy-1-carboxylic acids to alkenes is carried out under the following conditions:
50 mM Tris-HCl pH 7.5
50 mM 3-sulfonyloxy-1-carboxylic acid Assays are incubated with shaking at 37-65° C. for 2-72 hours in 2 ml sealed glass vials (Interchim). At the end of incubation one ml of the gaseous phase is collected and injected into a gas chromatograph Varian 430-GC equipped with a flame ionization detector (FID). Alkenes are identified by comparison with standard.

Example 7: Thermal Conversion of 3-sulfonyloxybutyrate to Propylene

Disodium (R,S)-3-sulfonyloxybutyrate was synthesized upon request by company specialized in custom synthesis, Syntheval (France).

The thermal conversion assays containing, in a total volume of 0.5 mL, 50 mM 3-sulfonyloxybutyrate and 50 mM Tris-HCl pH 7.5, were incubated in 2 ml sealed glass vials (Interchim) at 37° C. and 65° C. with shaking. Propylene production at different incubation times (from 0 to 90 h) was analyzed as follows. One ml of the gaseous phase was collected and injected into a gas chromatograph Varian 430-GC equipped with FID detector. Nitrogene was used as carrier gas with a flow rate of 1.5 ml/min. Volatile compounds were separated on RT-Alumina Bond/Na2SO4 column (Restek) using an isothermal mode at 130° C. Gaseous product of thermal decomposition of disodium (R,S)-3-sulfonyloxybutyrate was identified by comparison with propylene standard (Sigma, Aldrich). Under these GC conditions, the retention time for propylene was 3.2 min. Significant production of propylene was observed at 65° C. as well at 37° C. (FIGS. 6 and 7).

Example 8: Thermal Conversion of 3-sulfonyloxy-3-methylbutyrate to Isobutene 3-sulfonyloxy-3-methylbutyrate is synthesized upon request by company specialized in custom synthesis, Syntheval (France).

The thermal conversion assays containing, in a total volume of 0.5 ml, 50 mM 3-sulfonyloxybutyrate and 50 mM Tris-HCl pH 7.5, are incubated in 2 ml sealed glass vials (Interchim) at 37° C. and 65° C. with shaking. Isobutene production at different incubation times is analyzed as follows. One ml of the gaseous phase is collected and injected into a gas chromatograph Varian 430-GC equipped with FID detector. Nitrogene is used as carrier gas with a flow rate of 1.5 ml/min. Volatile compounds are separated on RT-Alumina Bond/Na2SO4 column (Restek) using an isothermal mode at 130° C. Gaseous product of thermal decomposition of 3-sulfonyloxy-3-methylbutyrate is identified by comparison with isobutene standard (Sigma, Aldrich).

Example 9: Enzyme Catalyzed Conversion of 3-sulfonyloxy-1-carboxylic acids to Corresponding Alkenes Enzyme catalyzed conversion of 3-sulfonyloxy-1-carboxylic acids to alkenes is carried out under the following conditions:
50 mM Tris-HCl pH 7.5
50 mM 3-sulfonyloxy-1-carboxylic acid
10 mM $MgCl_2$
5-10 mg/ml enzyme Assays are incubated with shaking at 37-42° C. for 2-72 h in 2 ml sealed glass vials (Interchim). At the end of incubation one ml of the gaseous phase is collected and injected into a gas chromatograph Varian 430-GC equipped with a flame ionization detector (FID). Alkenes are identified by comparison with standards.

Example 10: Enzyme Catalyzed Conversion of 3-sufonyloxybutyrate into Propylene Disodium (R,S)-3-sulfonyloxybutyrate was synthesized upon request by the custom chemist Syntheval.

Enzyme catalyzed conversion of 3-sufonyloxybutyrate into propylene is carried out under the following conditions:
50 mM Tris-HCl pH 7.5
0-100 mM Disodium (R,S)-3-sulfonyloxybutyrate
10 mM $MgCl_2$
5-10 mg/ml enzyme Assays are incubated with shaking at 37-42° C. for 2-72 h in 2 ml sealed glass vials (Interchim). At the end of incubation one ml of the gaseous phase is collected and injected into a gas chromatograph Varian 430-GC equipped with a flame ionization detector (FID). Propylene is identified by comparison with propylene standard (Sigma-Aldrich).

Example 11: Enzyme Catalyzed Conversion of 3-sulfonyloxy-3-methylbutyrate into Isobutene 3-sulfonyloxy-3-methylbutyrate is synthesized upon request by the custom chemist Syntheval.

Enzyme catalyzed conversion of 3-sulfonyloxy-3-methylbutyrate into isobutene is carried out under the following conditions:
50 mM Tris-HCl pH 7.5
0-100 mM 3-sulfonyloxy-3-methylbutyrate
10 mM $MgCl_2$
5-10 mg/ml enzyme Assays are incubated with shaking at 37-42° C. for 2-72 h in 2 ml sealed glass vials (Interchim). At the end of incubation one ml of the gaseous phase is collected and injected into a gas chromatograph Varian 430-GC equipped with a flame ionization detector (FID). Isobutene is identified by comparison with isobutene standard (Sigma-Aldrich).

The invention claimed is:
1. A method for producing an alkene from a 3-hydroxy-1-carboxylic acid comprising enzymatically converting, using a sulfotransferase, a 3-hydroxy-1-carboxylic acid of the following general formula I:

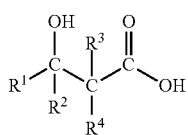
Formula I into a 3-sulfonyloxy-1-carboxylic acid of the following general formula II:

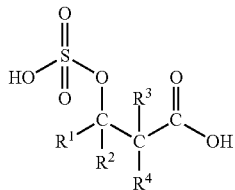
Formula II and then converting the 3-sulfonyloxy-1-carboxylic acid by thermal conversion into an alkene of the following general formula III:

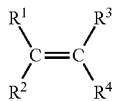
Formula III wherein $R^1$ and $R^3$ are independently selected from hydrogen (—H), methyl (—CH3), ethyl (—CH2-CH3), isopropyl (—CH2(CH3)2), vinyl (—CH=CH2) and isopropenyl (—C(CH3)=CH2) and in which $R^2$ and $R^4$ are independently selected from hydrogen (—H) and methyl (—CH3).

2. The method of claim 1, wherein the sulfotransferase is selected from alcohol sulfotransferase (EC 2.8.2.2), steroid sulfotransferase (EC 2.8.2.15), scymnol sulfotransferase (EC 2.8.2.32) flavonol 3-sulfotransferase (EC 2.8.2.25), retinol sulfotransferase/dehydratase, polyketide synthase (PKS) sulfotransferase or an olefin synthase (OLS) sulfotransferase.

3. The method of claim 1, wherein the method is carried out in vitro.

4. The method of claim 1, wherein the method is carried out in the presence of a microorganism or a plant producing the sulfotransferase.

5. The method of claim 1, further comprising a step of collecting the alkene produced in a gaseous state.

6. The method of claim 1 wherein the method is carried out in the presence of a composition comprising the sulfotransferase and a 3-hydroxy-1-carboxylic acid of formula I.

7. The method of claim 1, wherein the thermal conversion is carried out at a temperature of 30° C. or higher.

8. The method of claim 1, wherein the thermal conversion is carried out at a temperature of 37° C. or higher.

9. The method of claim 1, wherein the thermal conversion is carried out at a temperature of 40° C. or higher.

10. The method of claim 1, wherein the thermal conversion is carried out at a temperature of 45° C. or higher.

11. The method of claim 1, wherein the thermal conversion is carried out at a temperature of 50° C. or higher.

12. The method of claim 1, wherein the thermal conversion is carried out at a temperature of 55° C. or higher.

13. The method of claim 1, wherein the thermal conversion is carried out at a temperature of 60° C. or higher.

14. The method of claim 1, wherein the thermal conversion is carried out at a temperature of 65° C. or higher.

15. The method of claim 1, wherein the method is carried out in the presence of a mesophilic microorganism producing the sulfotransferase.

16. The method of claim 15, wherein the mesophilic organism is *E. coli*.

* * * * *